(12) United States Patent
Mustaev et al.

(10) Patent No.: US 9,415,111 B2
(45) Date of Patent: Aug. 16, 2016

(54) DUAL-SENSITIZER-CONTAINING LUMINESCENT COMPOUNDS, CONJUGATES, AND USES THEREOF

(75) Inventors: Arkady Mustaev, New York, NY (US); Salvatore A. E. Marras, Roselle Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1457 days.

(21) Appl. No.: 12/377,199

(22) PCT Filed: Aug. 11, 2007

(86) PCT No.: PCT/US2007/075761
§ 371 (c)(1),
(2), (4) Date: May 8, 2009

(87) PCT Pub. No.: WO2008/019403
PCT Pub. Date: Feb. 14, 2008

(65) Prior Publication Data
US 2010/0178251 A1    Jul. 15, 2010

Related U.S. Application Data

(60) Provisional application No. 60/822,235, filed on Aug. 12, 2006, provisional application No. 60/822,219, filed on Aug. 11, 2006.

(51) Int. Cl.
*A61K 47/48* (2006.01)
*A61K 49/00* (2006.01)
*G01N 33/58* (2006.01)

(52) U.S. Cl.
CPC ......... *A61K 47/48115* (2013.01); *A61K 47/481* (2013.01); *A61K 49/0019* (2013.01); *A61K 49/0021* (2013.01); *G01N 33/582* (2013.01); *G01N 2458/30* (2013.01); *G01N 2458/40* (2013.01)

(58) Field of Classification Search
CPC ............ A61K 47/481; A61K 49/0019; A61K 49/0021; A61K 47/48115; G01N 2458/40; G01N 33/582; G01N 2458/30
USPC ...................... 424/9.6; 514/253.08
See application file for complete search history.

(56) References Cited

U.S. PATENT DOCUMENTS

| | | | |
|---|---|---|---|
| 5,179,096 A * | 1/1993 | Gentilini et al. | 514/253.08 |
| 5,220,000 A | 6/1993 | Theodoropulos | |
| 5,639,615 A | 6/1997 | Selvin et al. | |
| 6,631,283 B2 | 10/2003 | Storrie et al. | |
| 2002/0058793 A1 | 5/2002 | Uray et al. | |
| 2005/0026813 A1 | 2/2005 | Olstein et al. | |
| 2005/0085413 A1 * | 4/2005 | Jin et al. | 514/8 |

FOREIGN PATENT DOCUMENTS

| | | |
|---|---|---|
| JP | 52-83382 A | 7/1977 |
| WO | 9303772 A1 | 3/1993 |

OTHER PUBLICATIONS

Gac-Breton et al., J. Drug Targeting, 2004, 12(5), p. 297-307.*
Ozaki, H. et al., Chem Lett., 2000, p. 312-313.*
Chen et al., Chinese Pharmaceutical Journal, 2005, 57, p. 57-70 (abstract).*
Veiopoulou et al., Analytica Chimica Acta, 1996, 335, p. 177-184.*
Rieutord et al., "Fluoroquinolones as sensitizers of lanthanide fluorescence: application to the liquid chromatographic determination of ciprofloxacin using terbium," Analytica Chimica Acta, Elsevier, Amsterdam, NL (May 20, 1994) 290 (1-2):215-225.
Tak et al., "Synthesis, characterization, electrochemistry and kinetics of CTDNA binding of a bis ciprofloxacin borate copper (II) complex," Transition Metal Chemistry (Oct. 1, 2002); 27(7):741-747.
Xiao et al., "Rationally designed, polymeric, extended metal-ciprofloxacin complexes," Chemistry—A European Journal (Nov. 4, 2005); 11(22): 6673-6686.
Chen et al., "Synthesis of 7-amino-4-trifluoromethyl-2-(1H)-quinolinone and its use as an antenna molecule for luminescent europium polyaminocarboxylates chelates," Journal of Photochemistry and Photobiology (Apr. 1, 2000); 135:27-32.
Selvin, P.R., "Crystal Structure and Spectroscopic Characterization of Luminescent Europium Chelate", Inorg. Chem. 1996, vol. 35, pp. 700-705.

* cited by examiner

*Primary Examiner* — Michael G Hartley
*Assistant Examiner* — Leah Schlientz
(74) *Attorney, Agent, or Firm* — Fox Rothschild LLP; Gerard P. Norton; W. Jerry Liu

(57) ABSTRACT

The invention relates to novel luminescent compositions of matter containing two fluorophores (sensitizers), synthetic methods for making the compositions, macromolecular conjugates of the compositions, and the use of the compositions and their conjugates in various methods of detection. The invention also provides kits containing the compositions and their conjugates for use in the methods of detection.

35 Claims, 16 Drawing Sheets

| Compound | UV Absorption | Luminescence of the corresponding TB³⁺ chelate |
|---|---|---|
| Cipro | Water: 38000<br>MeOH: 36000 | +++ |
| Cipro-AcBr | Water: 38000<br>MeOH: 38000 | ++ |
| EDTA-Cipro | Water: 38000<br>MeOH: 38000 | ++ |
| EDTA-(Cipro)₂ | Water: 48600<br>MeOH: 76000 | +++++ |

Figure 10a.

DUAL-SENSITIZER-CONTAINING LUMINESCENT COMPOUNDS, CONJUGATES, AND USES THEREOF

CROSS REFERENCE TO RELATED APPLICATIONS

This application is a National Stage of International Application No. PCT/US07/075761, filed Aug. 11, 2007, which claims priority under 35 U.S.C. §119(e) to U.S. Provisional Application Ser. No. 60/822,235, filed Aug. 12, 2006 and U.S. Provisional Application Ser. No. 60/822,219, filed Aug. 11, 2006, the disclosures of all three of which are incorporated herein by reference.

BACKGROUND OF THE INVENTION

Luminescent lanthanide chelates have become a primary focus of investigation due to their highly unusual spectral properties (Gudgin-Dickson et al. (1995) Pharmac. Ther. 66:207-235; Selvin, P. R. (2002) Annu. Rev. Biophys. Biomol. Struct. 31:275-302; and Hemmila et al. (2005) J. Fluoresc. 15:529-542). These molecules have been used in wide variety of biochemical assays, including, for example, medical diagnostics, drug discovery, and as imaging tools in cell biological applications. Luminescent lanthanide chelates are especially useful as non-isotopic alternatives to conventional organic fluorophores in the applications where high background fluorescence is an issue. The unusual spectral (i.e., sharply spiked peaks) and temporal (i.e., long lasting emissions) properties of the luminescent lanthanide chelates can allow for (i) ultra-high sensitivity of detection (ii) facile, simultaneous monitoring of several analytes in the same sample mixture, and (iii) more information to be obtained from a given individual analyte in a sample.

A lanthanide probe can contain, for example, an organic fluorophore and a caged, or chelated lanthanide. The fluorophore moiety acts as an antenna, or sensitizer, which absorbs the energy of the excitation light and transfers it to the lanthanide in a radiation-less fashion. The antenna is required to "pump," or activate the metal, since the absorbance of the lanthanide moiety is very low. The antenna-to-lanthanide energy transfer occurs only over a short distance (on the order of a few angstroms), which generally requires that the two moieties be tethered together.

Unfortunately, however, the process by which the fluorophore enhances lanthanide luminescence is not fully understood, which makes the optimization of the probe and its components difficult.

Despite a great demand for lanthanide probes for their use in a growing number of biologic assays, researchers often encounter a cost limitation. Such probes can cost up to $10,000 per mg, which is due, in large part, to laborious synthetic procedures. Thus not only is their a strong, unmet need for novel, more reactive, and more functionally delineated luminescent lanthanide probes, but also for cost-effective synthetic strategies that would allow for greater access to these reagents.

SUMMARY OF THE INVENTION

Provided herein is a composition of matter, which includes: (i) a first sensitizer moiety; (ii) a chelating moiety covalently joined, optionally through a first linker, to the first sensitizer; and (iii) a second sensitizer moiety covalently joined, optionally through a second linker, to the chelating moiety of (ii); wherein, the first and second sensitizer moiety, independently, have the Formula (I) or the Formula (II), wherein Formula (I) is:

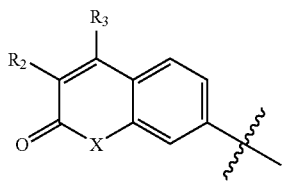

and wherein:

X is CH—$R_1$, O, S, or N—$R_1$;

$R_1$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_2$ is H; $NH_2$; carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and wherein the

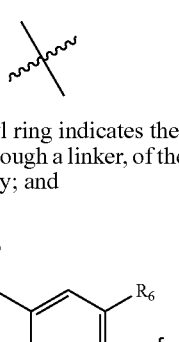

at position 7 of the phenyl ring indicates the site of covalent attachment, optionally through a linker, of the sensitizer moiety to the chelating moiety; and wherein Formula (II) is:

and wherein:

Z is a CH—$R_4$, O, S, or N—$R_4$;

$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms;

$R_5$ is carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and $R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene or alkylarene moieties are optionally further substituted with from 1-3 halo atoms; and wherein the

at position 7 of the phenyl ring indicates the site of covalent attachment, optionally through a linker, of the sensitizer moiety to the chelating moiety.

In one embodiment, the composition of matter includes formula I wherein X is an O atom. The composition can also have the formula I where $R_3$ is $CH_3$. In other embodiments, the composition of matter can have a first or second sensitizer moiety or a first and second sensitizer moiety with the formula:

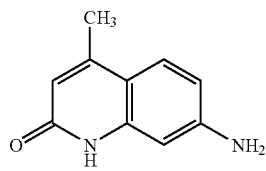

In another embodiment, the composition of matter includes formula I wherein X is O and $R_3$ is $CF_3$. In other embodiments, the composition of matter can have a first or second sensitizer moiety, or a first and second sensitizer moiety with the formula:

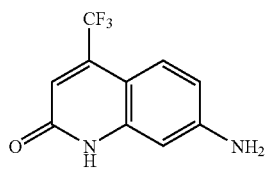 [SMILES: Nc1ccc2c(C(F)(F)F)cc(=O)[nH]c2c1]

In another embodiment, the composition of matter includes formula I wherein X is N—$R_1$ atom. The composition of matter can also have formula I where $R_1$ is H, and $R_3$ is $CF_3$. In some embodiments, the composition of matter can have a first or second sensitizer moiety, or a first and second sensitizer moiety having the formula:

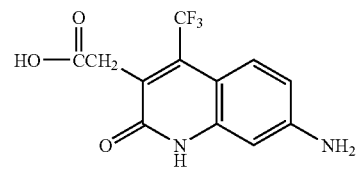

In another embodiment, the composition of matter includes formula II wherein Z is N—$R_4$. The composition of matter can also have the formula II where $R_4$ is a cyclopropyl moiety. The composition of matter can also have the formula II where $R_5$ is an organic acid moiety having the formula COOH and/or where $R_6$ is an F atom. In some embodiments, the composition of matter can have a first or second sensitizer moiety, or a first and second sensitizer moiety having the formula:

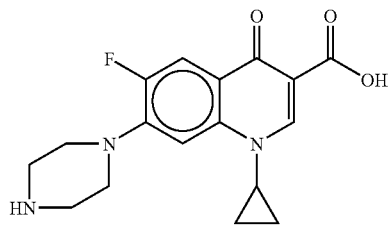

In some embodiments, the composition of matter can contain a chelating moiety including EDTA, DTPA, TTHA, DOTA, TAGA, DOTP, DTPA-BMA, DO2P, and HP-DO3A.

In some embodiments, the composition of matter can have one or both of the sensitizer moieties covalently linked at the $R_2$ or $R_5$ position, optionally through a third linker moiety, to a conjugating group. The conjugating group can have the chemical formula S=C=N— or Br—$CH_2$—CO—.

In embodiments where the composition of matter is a luminescent composition or luminescent chelate, the composition can further contain a metal ion chelated to the chelating moiety. The chelated metal ion can be a lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV).

In other embodiments, the compositions of matter can be conjugated to a macromolecule. The macromolecule can be a polypeptide (e.g., an antigen or antigen-binding fragment thereof, or a polypeptide ligand for a cellular receptor), or a nucleic acid (e.g., DNA or RNA).

Also provided herein are pharmaceutical compositions containing any of the compositions of matter described herein and a pharmaceutically acceptable carrier.

Featured herein is an in vitro method of detecting a target with a probe. The method includes the steps of: contacting a sample with a luminescent probe composition, which includes a targeting-probe moiety having an affinity for a target, the targeting-probe moiety covalently conjugated to a luminescent chelate composition comprising: (i) a first sensitizer moiety; (ii) a chelating moiety covalently joined, optionally through a first linker, to the first sensitizer; and (iii) a second sensitizer moiety covalently joined, optionally through a second linker, to the chelating moiety of (ii); wherein, the first and second sensitizer moiety, independently, have the Formula (I) or the Formula (II), wherein Formula (I) is:

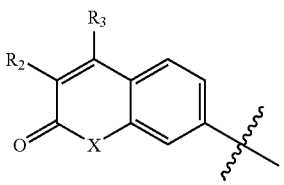

and wherein:

X is CH—$R_1$, O, S, or N—$R_1$;

$R_1$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_2$ is H; $NH_2$; carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and wherein the

at position 7 of the phenyl ring indicates the site of covalent attachment, optionally through a linker, of the sensitizer moiety to the chelating moiety; and wherein Formula (II) is:

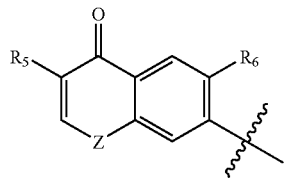

and wherein:

Z is CH—$R_4$, O, S, or N—$R_4$;

$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene moieties are optionally further substituted with from 1-3 halo atoms;

$R_5$ is carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and $R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene or alkylarene moieties are optionally further substituted with from 1-3 halo atoms; and wherein the

position 7 of the phenyl ring indicates the site of covalent attachment, optionally through a linker, of the sensitizer moiety to the chelating moiety; and wherein the chelating moiety is selected from the group consisting of: EDTA, DTPA, TTHA, DOTA, TAGA, DOTP, DTPA-BMA, DO2P, and HP-DO3A; and wherein one of the sensitizer moieties is covalently linked at the $R_2$ or $R_5$ position, optionally through a third linker moiety, to a conjugating group; and wherein the luminescent composition further comprises a lanthanide chelated to the chelating moiety, the lanthanide selected from the group consisting of: Gd(III), Dy(III), Ho(III), Er(III), Eu(III), Tm(III), Sm(III), Ce(III), Pr(III), Yb(III), Tm(III), Nd(III), and Tb(IV); and detecting a signal produced from the luminescent probe composition.

The sample can contain one or more cells, cellular material (e.g., a whole cell lysate), or can contain one or more purified and/or recombinant protein. The sample can also contain only buffer (e.g., phosphate-buffered saline) (e.g., where the sample is used as a negative control). The luminescent probe composition can contain any of the luminescent chelate compositions described herein. The subject can be any subject described herein (see below). Detection can include detecting luminescence emissions from the luminescent probe composition, detecting fluorescence emissions from one or both sensitizers of the luminescent probe composition, or detecting both luminescence and fluorescence emissions from the luminescent probe composition.

Also featured herein is an in vivo method of detecting a target with a probe, the method comprising: delivering to a subject a luminescent probe composition comprising a targeting-probe moiety having an affinity for a target, the targeting-probe moiety covalently conjugated to a luminescent chelate composition comprising: (i) a first sensitizer moiety; (ii) a chelating moiety covalently joined, optionally through a first linker, to the first sensitizer; and (iii) a second sensitizer moiety covalently joined, optionally through a second linker, to the chelating moiety of (ii); wherein, the first and second sensitizer moiety, independently, have the Formula (I) or the Formula (II), wherein Formula (I) is:

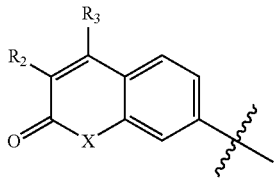

and wherein:
X is CH—$R_1$, O, S, or N—$R_1$;
$R_1$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;
$R_2$ is H; $NH_2$; carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene moieties are optionally further substituted with from 1-3 halo atoms; and
wherein the

at position 7 of the phenyl ring indicates the site of covalent attachment, optionally through a linker, of the sensitizer moiety to the chelating moiety; and
wherein Formula (II) is:

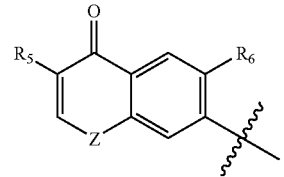

and wherein:
Z is CH—$R_4$, O, S, or N—$R_4$;
$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$, a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms;
$R_5$ is carboxamide; hydrazide; acylhydrazide or alkylhydrazide; hydroxamate; COOH; CO—R' or CO—O—R', where R' is a linear alkylene ($C_1$-$C_{29}$), a branched alkylene ($C_3$-$C_{29}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{29}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;
$R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{10}$, an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and wherein the

at position 7 of the phenyl ring indicates the site of covalent attachment, optionally through a linker, of the sensitizer moiety to the chelating moiety; and wherein the chelating moiety is selected from the group consisting of: EDTA, DTPA, TTHA, DOTA, TAGA, DOTP, DTPA-BMA, DO2P, and HP-DO3A; and wherein one of the sensitizer moieties is covalently linked at the $R_2$ or $R_5$ position, optionally through a third linker moiety, to a conjugating group; and wherein the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV); and detecting a signal produced from the luminescent probe composition.

The luminescent probe composition can contain any of the luminescent chelate compositions described herein. The subject can be any subject described herein (see below). Detection can include detecting luminescence emissions from the luminescent probe composition, detecting fluorescence emissions from one or both sensitizers of the luminescent probe composition, or detecting both luminescence and fluorescence emissions from the luminescent probe composition.

Provided herein is a luminescently labeled hairpin-forming oligonucleotide consisting of: (a) a luminescent composition comprising: (i) a first sensitizer moiety; (ii) a chelating moiety covalently joined, optionally through a first linker, to the first sensitizer; and (iii) a second sensitizer moiety covalently joined, optionally through a second linker, to the chelating moiety of (ii); wherein, the first and second sensitizer moiety, independently, have the Formula (I) or the Formula (II), wherein Formula (I) is:

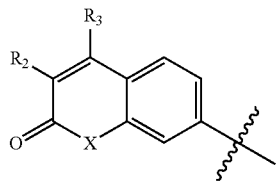

and wherein:
X is CH—$R_1$, O, S, or N—$R_1$;
$R_1$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_2$ is H; $NH_2$; carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and wherein the

at position 7 of the phenyl ring indicates the site of covalent attachment, optionally through a linker, of the sensitizer moiety to the chelating moiety; and
wherein Formula (II) is:

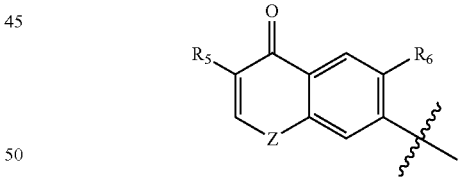

and wherein:
Z is CH—$R_4$, O, S, or N—$R_4$;
$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms;

$R_5$ is carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene or alkylarene moieties are optionally further substituted with from 1-3 halo atoms; and wherein the

position 7 of the phenyl ring indicates the site of covalent attachment, optionally through a linker, of the sensitizer moiety to the chelating moiety; and wherein the chelating moiety is selected from the group consisting of: EDTA, DTPA, TTHA, DOTA, TAGA, DOTP, DTPA-BMA, DO2P, and HP-DO3A; and wherein one of the sensitizer moieties is covalently linked at the $R_2$ or $R_5$ position, optionally through a third linker moiety, to a conjugating group; and wherein the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV); the luminescent composition covalently conjugated to a hairpin-forming oligonucleotide; and (b) a quencher moiety capable of quenching the fluorescence of either or both of (i) either or both sensitizer moieties, or (ii) the luminescence of the lanthanide moiety, wherein the quencher moiety is covalently conjugated to the hairpin-forming oligonucleotide; the oligonucleotide having a closed conformation including a single-stranded loop and a stem duplex formed by complementary 3' and 5' arms, wherein the quencher moiety is in a quenching relationship to at least one of the lanthanide or sensitizer moieties; wherein, when excited at the maximum excitation wavelength of one or both of the sensitizer moieties, emission at the maximum emission wavelength of one or both of the sensitizer moieties is substantially suppressed relative to the unquenched magnitude and emission at the maximum emission wavelength of the one or both of the sensitizer moieties; and the oligonucleotide having an open conformation, not including the stem duplex, in which the quencher moiety is not in a quenching relationship with the lanthanide or the first or second, or first and second sensitizer moieties;

wherein, when excited at the maximum excitation wavelength of one or both of the first and second sensitizer moieties, the luminescence of the lanthanide moiety increases due to fluorescence resonance energy transfer from one or both of the sensitizer moieties.

Hybridization of the loop to a target nucleotide can cause the oligonucleotide to assume its open confirmation. The quencher moiety is selected from the group consisting of BHQ, DABCYL, and variants of DABCYL. The single-stranded loop and one strand of the stem duplex can be complementary to the target strand, whereby the oligonucleotide is capable of serving as a primer for DNA polymerase. The oligonucleotide can also include a terminal extension capable of serving as a priming region for a DNA polymerase when the oligonucleotide is in its closed conformation.

Also featured herein is a reagent kit for nucleic acid amplification including ingredients for a nucleic acid amplification, a detector probe that is any of the conjugated oligonucleotides described herein, and instructions for carrying out the amplification reaction. Nucleic acid amplification can be polymerase chain reaction (PCR), strand displacement amplification (SDA), transcription-mediated amplification (TMA), ligase chain reaction (LCR), nucleic acid sequence based amplification (NASBA), rolling circle amplification, loop-mediated isothermal amplification (LAMP), or amplification of RNA by an RNA-directed RNA polymerase.

The invention also features a reagent kit for an amplification reaction including ingredients for an amplification reaction that includes at least one primer (e.g., any of the luminescently labeled hairpin-forming oligonucleotide conjugates described herein), ingredients for the amplification assay and instructions for carrying out the amplification assay. Nucleic acid amplification can be polymerase chain reaction (PCR), strand displacement amplification (SDA), transcription-mediated amplification (TMA), ligase chain reaction (LCR), nucleic acid sequence based amplification (NASBA), rolling circle amplification, loop-mediated isothermal amplification (LAMP), or amplification of RNA by an RNA-directed RNA polymerase.

Also featured herein is a detection assay which includes the steps of adding to a sample that can optionally contain a target strand at least one detector probe that is any luminescently labeled hairpin-forming oligonucleotide conjugate described herein and detecting luminescence emission from the at least one detector probe's luminescent chelate moiety. The detection can also include detecting fluorescence emission from one or both of the at least one probe's fluorescent sensitizer moieties.

Also provided is an amplification assay that includes the steps of adding to a sample that can optionally contain a target strand the reagents to perform any amplification reaction described herein at least one of any of the luminescently labeled hairpin-forming oligonucleotide conjugates described herein, and detecting luminescence and/or fluorescence emission from the luminescent chelate moiety of the at least one of any of the luminescently labeled hairpin-forming oligonucleotide conjugates described herein.

Also provided herein is a synthetic method of making a chemically-conjugatable fluorophore compound. The method includes the steps of: (a) reacting trifluoroacetylmethylethylsuccinate with 1,3 phenylenediamine; and (b) saponifying the product of (a) to generate a free carboxylate group on the product for coupling with a polymethylenediamine group. In one embodiment, the method further includes: (c) reacting the product of (b) with 4-nitrophenol and coupling with a polymethylenediamine group. In another embodiment, the method further includes treating the product of (c) with an activated ester of halogenoacetic acid or thiocarbonyldiimidazole. An additional embodiment includes: (d) reacting the product of (c) with $R_e$—$X_a$, wherein $R_e$ is a rare-earth chelating compound and $X_a$ is COOH or an anhydride thereof. In yet another embodiment, the method includes: (e) reacting the product of (d) with DTPA dianhydride. In another embodiment, the method includes reacting the product of (e) with a water-soluble lanthanide salt selected from Gd(III), Dy(III), Ho(III), Er(III), Eu(III), Tb(III), Sm(III), Ce(III), Pr(III), Yb(III), Tm(III), Nd(III), and Tb(IV).

The details of one or more embodiments of the invention are set forth in the accompanying drawings and the description below. Other features, objects, and advantages of the invention will be apparent from the description and drawings, and from the claims. All cited patents, patent applications, and references are incorporated by reference in their entireties for all purposes.

In case of conflict, the present specification, including definitions, will control. In addition, the materials, methods, and examples are illustrative only and not intended to be limiting.

DETAILED DESCRIPTION OF THE INVENTION

Figure 1:
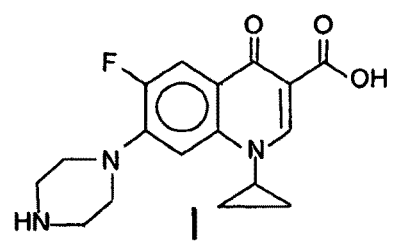
FIG. 1 is a depiction of the chemical structures of several of the sensitizer moieties described herein. (I) ciprofloxacin, (II) cs124, (III) $CF_3$-124, (IV) 3-carboxymethyl $CF_3$-cs124.
Figure 1:
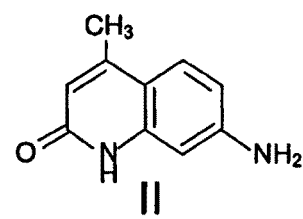
Figure 1:
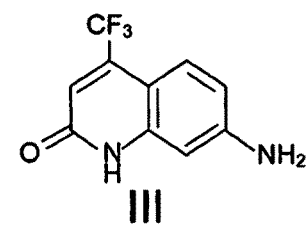
Figure 1:
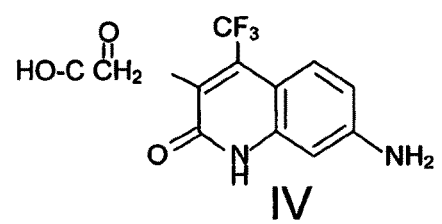

Featured herein are compositions of matter and macromolecular conjugates of the compositions, as well as methods of use for the compositions and their conjugates. Various aspects of the invention are described below.

Definitions

The term "subject" refers to a member of the class Mammalia. Examples of mammals include, without limitation, humans, primates (e.g., chimpanzees, monkeys, baboons), rodents (e.g., mice, rats, rabbits, guinea pigs, horses, livestock, dogs, cats, sheep, and cows. In certain preferred embodiments, the "subject" is a human (e.g., a human patient).

As used herein, "macromolecule" refers to a molecule with a large molecular mass, composed of much larger numbers (hundreds or thousands) of atoms than ordinary molecules. Some macromolecules are individual entities that cannot be subdivided without losing their identity (e.g., certain proteins, certain nucleic acids). Others (e.g., polymers) are multiples of a repeating building block (monomer) in chains or networks (e.g., plastics, cellulose). Examples of such macromolecules include, but are not limited to, polypeptides (protein complexes), nucleic acids (e.g., DNA and RNA), polymers (e.g., polystyrene, polyethylene, cellulose (i.e., sugar polymers)). The term macromolecule also refers to complexes of two or more polypeptides or nucleic acids (e.g., a protein dimer, or a double-stranded DNA molecule).

As used herein, the term "probe" refers to a molecule that constitutes one member of a binding pair, wherein the other member of the binding pair is the "target" of the probe. The molecule can be a small molecule (e.g., a compound), a macromolecule (e.g., an antibody, a nucleic acid; see above). For example, where the probe is an antibody, the target is the antigen (e.g., the antigen containing the epitope) that the antibody specifically recognizes. Where the probe is a ligand, the target is the cognate receptor the ligand specifically binds to (e.g., Epidermal Growth Factor (EGF) ligand binding to EGF-Receptor). Where the probe is a nucleic acid (e.g., a DNA probe), the target is a complementary nucleic acid sequence to the nucleic acid probe. Where the probe is a polypeptide, the polypeptide can be of any length or function. Where the probe is a compound, the target can be, e.g., a receptor (e.g., a steroid or hormone receptor (e.g., the estrogen receptor) or a enzyme target (e.g., a kinase) where the compound binds to or inhibits the enzyme target. The polypeptide can also be a polypeptide that is encoded or expressed in any species or biological organism (e.g., a bacterial protein, a viral protein, an insect protein, a nematode protein, a mammalian protein, a human protein). The polypeptide can also be naturally produced by an organism or can be made synthetically (e.g., by automated chemical synthesis).

As used herein, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, pharmaceutically acceptable derivatives of a composition for use in any of the in vivo methods described herein include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl or heterocyclyl.

Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" carbon chains, if not specified, contain from 1 to 20 (e.g., 1, 2, 3, 4, 5, 6, 7, 8, 9, 10, 11, 12, 13, 14, 15, 16, 17, 18, 19, or 20; 1-5, 1-6, 1-10, 10-15, 15-20) carbons and are straight, cyclic, or branched. Alkenyl carbon chains of from 2 to 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbons, in certain embodiments, contain 1 to 8 (e.g., 1, 2, 3, 4, 5, 6, 7, or 8) double bonds and alkenyl carbon chains of 2 to 16 (e.g., 2, 3, 4, 5, 6, 7, 8, 9, 10, 11, 12, 13, 14, 15, or 16) carbons, in certain embodiments, contain 1 to 5 (e.g., 1, 2, 3, 4, or 5) double bonds. Alkynyl carbon chains of from 2 to 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbons, in certain embodiments, contain 1 to 8 triple bonds, and the alkynyl carbon chains of 2 to 16 (e.g., 2, 3, 4, 5, 6, 7, 8, 9, 10, 11, 12, 13, 14, 15, or 16) carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons (e.g., 1, 2, 3, 4, 5, or 6). As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 (e.g., 3, 4, 5, 6, 7, 8, 9, or 10; 3-5, 3-6, 3-8, 5-10) carbon atoms, in other embodiments of 3 to 6 (e.g., 3, 4, 5, or 6) carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 (e.g., 3, 4, 5, 6, 7, 8, 9 or 10; 3-5, 3-7, 5-10) carbon atoms, with cycloalkenyl groups, in further embodiments, containing 4 to 7 (e.g., 4, 5, 6, or 7) carbon atoms and cycloalkynyl groups, in further embodiments, containing 8 to 10 (e.g., 8, 9 or 10) carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" or "arene" refers to aromatic monocyclic or multicyclic groups containing from 6 to 19 (e.g., 6, 7, 8, 9, 10, 11, 12, 13, 14, 15, 16, 17, 18, or 19; 6-8, 6-10, 6-12, 6-15, 10-15, 15-19) carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 (e.g., 5, 6, 7, 8, 9, 10, 11, 12, 13, 14, or 15; 5-7, 5-9, 5-10, 10-12, 10-15) members where one or more, in one embodiment 1 to 3 (e.g., 1, 2, or 3), of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a monocyclic or multicyclic non-aromatic ring system, in one embodiment of 3 to 10 (e.g., 3, 4, 5, 6, 7, 8, 9, or 10) members, in another embodiment of 4 to 7 (e.g., 4, 5, 6, or 7) members, in a further embodiment of 5 to 6 members, where one or more, in certain embodiments, 1 to 3 (e.g., 1, 2, or 3), of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "sulfinyl" or "thionyl" refers to $-S(O)-$.
As used herein, "sulfonyl" or "sulfuryl" refers to $-S(O)_2-$.
As used herein, "sulfo" refers to $-S(O)_2O-$.

As used herein, "carboxy" refers to a divalent radical, $-C(O)O-$.

As used herein, "aminocarbonyl" refers to $-C(O)NH_2$.

As used herein, "arylaminocarbonyl" refers to $-C(O)NHR$ in which R is aryl, including lower aryl, such as phenyl.

As used herein, "hydroxycarbonyl" refers to $-COOH$.

As used herein, "alkylene" refers to a straight, branched or cyclic, in certain embodiments straight or branched, divalent aliphatic hydrocarbon group, in one embodiment having from 1 to about 20 carbon atoms (e.g., 1, 2, 3, 4, 5, 6, 7, 8, 9, 10, 11, 12, 13, 14, 15, 16, 17, 18, 19, or 20, or 1-2, 1-5, 1-10, 6-10, 10-15, or 10-20). In a further embodiment alkylene includes lower alkylene. There may be optionally inserted along the alkylene group one or more oxygen, sulfur, including $S(=O)$ and $S(=O)_2$ groups, or substituted or unsubstituted nitrogen atoms, including $-NR-$ and $-N^+RR-$ groups, where the nitrogen substituent(s) is(are) alkyl, aryl, aralkyl, heteroaryl, heteroaralkyl or COR', where R' is alkyl, aryl, aralkyl, heteroaryl, heteroaralkyl, $-OY$ or $-NYY$, where Y is hydrogen, alkyl, aryl, heteroaryl, cycloalkyl or heterocyclyl. Alkylene groups include, but are not limited to, methylene ($-CH_2-$), ethylene ($-CH_2CH_2-$), propylene ($-(CH_2)_3-$), methylenedioxy ($-O-CH_2-O-$) and ethylenedioxy ($-O-(CH_2)_2-O-$). The term "lower alkylene" refers to alkylene groups having 1 to 6 (e.g., 1, 2, 3, 4, 5, or 6) carbons. In certain embodiments, alkylene groups are lower alkylene, including alkylene of 1 to 3 (e.g., 1, 2, or 3) carbon atoms.

As used herein, "alkenylene" refers to a straight, branched or cyclic, in one embodiment straight or branched, divalent aliphatic hydrocarbon group, in certain embodiments having from 2 to about 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbon atoms and at least one double bond, in other embodiments 1 to 12 (e.g., 1, 2, 3, 4, 5, 6, 7, 8, 9, 10, 11, or 12; 1-5, 2-6, 2-10, or 10-12) carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, $-CH=CH-CH=CH-$ and $-CH=CH-CH_2-$. The term "lower alkenylene" refers to alkenylene groups having 2 to 6 (e.g., 2, 3, 4, 5, or 6) carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, $-C\equiv C-C\equiv C-$, $-C\equiv C-$ and $-C\equiv C-CH_2-$. The term "lower alkynylene" refers to alkynylene groups having 2 to 6 (e.g., 2, 3, 4, 5, or 6) carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbon atoms and at least one triple bond, and at least one double bond; in another embodiment 1 to 12 (e.g., 1, 2, 3, 4, 5, 6, 7, 8, 9, 10, 11, or 12; 1-5, 2-6, 2-10, or 10-12) carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, $-C\equiv C-(CH_2)_n-C\equiv C-$, where n is 1 or 2. The term "lower alk(en)(yn)ylene" refers to alk(en)(yn)ylene groups having up to 6 (e.g., 1, 2, 3, 4, 5, or 6) carbons. In certain embodiments, alk(en)(yn)ylene groups have about 4 (e.g., 1, 2, 3, or 4) carbon atoms.

As used herein, "cycloalkylene" refers to a divalent saturated mono- or multicyclic ring system, in certain embodiments of 3 to 10 (e.g., 3, 4, 5, 6, 7, 8, 9, or 10; 3-5, 3-6, 3-10, or 6-10) carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 (e.g., 5, 6, 7, 8, 9, 10, 11, 12, 13, 14, or 15; 5-8, 5-10, 8-12, or 10-15) atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from Q1.

As used herein, isothiocyanate (ITC) refers to a —N=C=S moiety.

Where the number of any given substituent is not specified (e.g., haloalkyl), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

The Compositions of Matter

The compositions and conjugates of the compositions provided herein are useful in any of the methods provided herein. In one embodiment, the compositions or conjugates thereof may be used in detection assay in vitro. In a related embodiment, the compositions and conjugates thereof may be used for diagnostic or detection methods in vivo.

In one embodiment, the compositions for use in the conjugates and methods provided herein include: (i) a first sensitizer moiety; (ii) a chelating moiety covalently joined, optionally through a first linker, to the first sensitizer; and (iii) a second sensitizer moiety covalently joined, optionally through a second linker, to the chelating moiety of (ii); wherein, the first and second sensitizer moiety, independently, have the Formula (I) or the Formula (II), wherein Formula (I) is:

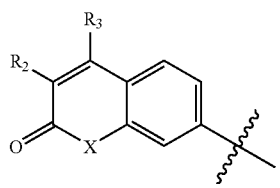

and wherein:
X is CH—$R_1$, O, S, or N—$R_1$;
$R_1$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_2$ is H; $NH_2$; carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and
wherein the

at position 7 of the phenyl ring indicates the site of covalent attachment, optionally through a linker, of the sensitizer moiety to the chelating moiety; and wherein Formula (II) is:

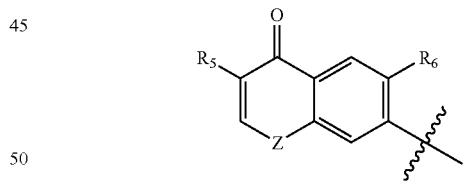

and wherein:
Z is a CH—$R_4$, O, S, or N—$R_4$;
$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms;

$R_5$ is carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and $R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene or alkylarene moieties are optionally further substituted with from 1-3 halo atoms; and
wherein the

at position 7 of the phenyl ring indicates the site of covalent attachment, optionally through a linker, of the sensitizer moiety to the chelating moiety.

In one embodiment, the above described composition contains one or both sensitizer moieties with the formula I or II where X is an O atom. In another embodiment, the above described composition contains one or both sensitizer moieties with the formula I or II where $R_3$ is $CH_3$. In certain embodiments, the above described composition contains one or both sensitizer moieties with the formula I or II where X is O and $R_3$ is $CH_3$.

In one embodiment, the above described composition contains one or both sensitizer moieties with the formula I or II and has the chemical formula of compound cs124 of FIG. 1.

In one embodiment, the above described composition contains one or both sensitizer moieties with the formula I or II where $R_3$ is $CF_3$. In another embodiment, the above described composition contains one or both sensitizer moieties with the formula I or II where X is O and $R_3$ is $CF_3$.

In certain embodiments, the above described composition contains one or both sensitizer moieties with the formula I or II and has the chemical formula of compound $CF_3$-cs124 of FIG. 1.

In one embodiment, the above described composition contains one or both sensitizer moieties with the formula I or II where X is N—$R_1$. In one embodiment, the above described composition contains one or both sensitizer moieties with the Formula I or II where X is N—H. In another embodiment, the above described composition contains one or both sensitizer moieties with the Formula I or II where $R_3$ is $CF_3$. In certain embodiments, the above described composition contains one or both sensitizer moieties with the Formula I or II where X is N—H, and $R_3$ is $CF_3$.

In certain embodiments, the above described composition contains one or both sensitizer moieties with the Formula I or II and has the chemical Formula of compound 3-carboxymethyl $CF_3$-cs124 of FIG. 1.

In another embodiment, the above described composition contains one or both sensitizer moieties with the Formula I or II where Z is an N atom and $R_4$ is a cyclopropyl moiety. In another embodiment, the above described composition contains one or both sensitizer moieties with the Formula I or II where $R_5$ is an organic acid moiety having the Formula COOH. In another embodiment, the above described composition contains one or both sensitizer moieties with the Formula I or II where Z is N—$R_4$, $R_4$ is a cyclopropyl moiety, and $R_5$ is an organic acid moiety having the Formula COOH. In another embodiment, the above described composition contains one or both sensitizer moieties with the Formula I or II where $R_6$ is an F atom. In a related embodiment, the above described composition contains one or both sensitizer moieties with the Formula I or II where Z is an N—$R_4$, $R_3$ is a cyclopropyl moiety, $R_5$ is an organic acid moiety having the Formula COOH, and $R_6$ is an F atom.

In certain embodiments, the above described composition contains one or both sensitizer moieties with the Formula I or II and has the chemical Formula of compound Ciprofloxacin as depicted in FIG. 1.

In various embodiments, any of the above described compositions contain a chelating moiety. Chelating moieties can be, but is not limited to, for example, EDTA, DTPA, TTHA, DOTA, TAGA, DOTP, DTPA-BMA, DO2P, and HP-DO3A.

In certain embodiments, the above described compositions contain the chelating moiety EDTA. In other embodiments, the above described compositions contain the chelating moiety DPTA.

In some embodiments, the above-described compositions have a first and second, or first or second linker moiety. In some embodiments, the above-described compositions have a first and second, or first or second linker moiety, where the first and second or first or second linker moiety, independently, have/has the Formula —NH—. In another embodiment, the above-described compositions have a first and second, or first or second linker moiety, where the first and second or first or second linker moiety, independently, is a heterocyclic alkylene moiety having the formula $N_2C_4H_8$, and where the covalent linkages occur through the N atoms.

In some embodiments, the chelating moiety is covalently joined to one or both of the sensitizer moieties or to one or both of the first and second linker moieties through a N atom of the chelating moiety. In other embodiments, the chelating moiety is covalently joined to one or both sensitizer moieties or to one or both of the first and second linker moieties through a carbonyl group of the chelating moiety.

In another embodiment, the above described compositions have a third linker moiety convalently joined to one or both sensitizer moieties. In some embodiments, the third linker moiety is joined at the $R_2$ position of one or both of the sensitizer moieties. In some embodiments, the third linker moiety is covalently joined to one or both sensitizer moieties at position 7. In some embodiments, the third linker moiety has the chemical formula —$(CH_2)_n$—, and n is an integer from 1 to 20 (e.g., 1, 2, 3, 4, 5, 6, 7, 8, 9, 10, 11, 12, 13, 14, 15, 16, 17, 18, 19, or 20; 1-3, 1-4, 1-5, 1-8, 1-10, 5-10, 5-12, 5-15, 10-15, 15-20). In certain embodiments, the third linker has Formula —$(CH_2)_n$— where n is 4. It is understood that the length of the linker moiety will depend on a variety of factors including, but not limited to, the macromolecule that can be covalently joined to the above described compositions.

In additional embodiments, any of the above described compositions containing a third linker, can be further covalently joined, through the third linker, to a conjugating group. Such a conjugating group is useful for covalently conjugating (i.e., joining) the compositions, for example, to macromolecules (e.g., nucleic acids or polypeptides).

In certain embodiments, the conjugating group has the Formula —S═C═N— or —C(O)—$CH_2$—Br.

In some embodiments, any of the above described compositions can further contain a metal ion. In certain embodiments, the metal ion is a trivalent metal ion. In certain embodiments, the metal ion can be, but is not limited to: Gd(III), Ho(III), Er(III), Eu(III), Tb(III), Sm(III), Ce(III), Pr(III), Yb(III), Tm(III), Nd(III), and Tb(IV). In certain embodiments, the metal ion is a lanthanide. In some embodiments, the metal ion is Tb(III) or Eu(III) (also referred to herein as $Tb^{3+}$ or $Eu^{3+}$ respectively).

Preparation of the Compounds

The compositions for use in the pharmaceutical compositions and methods provided herein can be prepared by the methods shown herein, or by routine modification of these methods using the appropriate starting materials. Specific methods for generating the compositions of matter described herein are detailed in the forthcoming examples below (see, Examples 1, 2, and 4).

In Vitro Methods of Detection

Provided herein are in vitro methods of detecting a target with a probe as well as compositions useful in the in vitro detection methods. The methods include the steps of: contacting a sample with a luminescent probe composition comprising a targeting-probe moiety having an affinity for a target, the targeting-probe moiety covalently conjugated to a luminescent chelate composition comprising: (i) a first sensitizer moiety; (ii) a chelating moiety covalently joined, optionally through a first linker, to the first sensitizer; and (iii) a second sensitizer moiety covalently joined, optionally through a second linker, to the chelating moiety of (ii); wherein, the first and second sensitizer moiety, independently, have the Formula (I) or the Formula (II), wherein Formula (I) is:

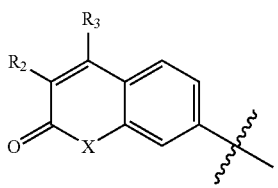

and wherein:

X is CH—$R_1$, O, S, or N—$R_1$;

$R_1$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_2$ is H; $NH_2$; carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and wherein the

at position 7 of the phenyl ring indicates the site of covalent attachment, optionally through a linker, of the sensitizer moiety to the chelating moiety; and wherein Formula (II) is:

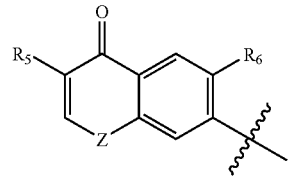

and wherein:

Z is CH—$R_4$, O, S, or N—$R_4$;

$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene moieties are optionally further substituted with from 1-3 halo atoms;

$R_5$ is carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and $R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene or alkylarene moieties are optionally further substituted with from 1-3 halo atoms; and wherein the

at position 7 of the phenyl ring indicates the site of covalent attachment, optionally through a linker, of the sensitizer moiety to the chelating moiety; and wherein the chelating moiety is selected from the group consisting of: EDTA, DTPA, TTHA, DOTA, TAGA, DOTP, DTPA-BMA, DO2P, and HP-DO3A; and wherein one of the sensitizer moieties is covalently linked at the $R_2$ or $R_5$ position, optionally through a third linker moiety, to a conjugating group; and wherein the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV); and detecting a signal produced from the luminescent probe composition.

In some instances, the methods and compositions can be useful for scientific research, for example, for identifying the subcellular localization (e.g., nuclear or cytoplasmic localization) of a new protein or known protein (e.g., NF-κB or p53). The methods and compositions can also be used, for example, to detect the infection of a cell by a virus, bacterium, or other infectious microbe in studies of infectivity (or prevention of infection) (see, for example, Tardif et al. (2003) J. Virol. 77(22):12299-309). Other research uses for the detection methods include detecting the presence of a particular polypeptide as expressed by a cell or by a tissue. Expression of the polypeptide can be protein or mRNA expression, and their differential detection using the appropriate conjugates (e.g., conjugates of the luminescent chelates and an antibody or nucleic acid) is described in detail below.

The methods and compositions can also be useful in conjunction with separation techniques including, but not limited to, cell-sorting (e.g., fluorescence-assisted cell sorting (FACS)), chromatography, or electrophoretic, osmotic, or centrifugal separations.

The in vitro detection methods and compositions can also be useful in diagnostic assays or tests to, for example, detect or screen for disease biomarkers present in a sample. Such compositions and methods can be used to diagnose patients through the analysis of patient samples (e.g., to detect evidence of viral or bacterial infection, or the presence of cancer cells) (see, for example, Boshell et al (2002) Biomedica 22(1):30-38). It is contemplated that samples (e.g., obtained or provided from a subject (e.g., a human patient)) can be blood, urine, lymph fluid, cerebral spinal fluid, amniotic fluid, vaginal fluid, semen and stool samples. Samples can also be obtained or provided from resected tissue or biopsy material including needle biopsy. Tissue section preparation for surgical pathology may be frozen and prepared using standard techniques. Immunohistochemistry and in situ hybridization binding assays on tissue sections are performed in fixed cells (see below). Cells may be isolated from fluid sample such as centrifugation. Numerous other techniques are available for obtaining tissue samples, and are well known to those in the art, for example, test samples can be obtained by such methods as withdrawing fluid with a syringe or by a swab.

In some embodiments of the compositions and method, the probe moiety covalently joined to a luminescent moiety is an antibody, or antigen-binding fragment of an antibody. Antibodies or antibody fragments that bind to specific target antigens of interest can be generated by immunization, e.g., using an animal, or by in vitro methods such as phage display. As used herein, "target antigen" refers to the antigen bearing the epitope that a specific antibody recognizes.

The imaging methods of the invention using the antibody-based probes, and their luminescent conjugates, embrace numerous modes of detection. In one embodiment, immunohistochemistry techniques can be used to identify and essentially stain cells with one or more antigens recognized by the conjugated antibodies. Such "staining" allows, for example, for analysis of viral or bacterial infection of a cell (e.g., if the antibody specifically recognizes an epitope in a bacterial or viral antigen) or to identify a normal versus a cancer cell (e.g., if the antibody recognizes an epitope specifically expressed in a normal or a cancer cell (e.g., a cancer cell expressing the Melanoma Antigen (MAGE)). Live or fixed cells can be contacted with antibodies specific for the target antigen (e.g., anti-MAGE antibodies), wherein the target antigen (e.g., MAGE), if present in the target cells (e.g., the melanoma cells), are recognized and bound by the antibodies. The primary antibodies (i.e., the antibodies that specifically recognize the antigen (e.g., the MAGE antigen) can be detectably labeled (covalently joined) directly with one or more of the luminescent moieties, or detection can occur using an secondary (anti-IgG) antibody or, for example, Protein-A or Protein-G that has been detectably labeled (covalently joined) with one or more luminescent moieties.

Detection of a polypeptide in a test sample is routine and one of ordinary skill in the art can detect the presence or absence of a protein or an antibody using well known methods. In another embodiment, the antibody probe conjugates described herein can be used in immunoassay methods to detect the presence of an antigen in a sample. According to some embodiments, immunoassays comprise allowing proteins in the sample to bind a solid phase support such as a plastic surface. Detectably-labeled antibodies (i.e., antibodies conjugated to the luminescent moieties) are then added and selectively bind to their cognate antigens. Detection of the detectable (i.e., luminescently-labeled) antibody indicates the presence of the antigen in the sample. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described, for example, in Voller et al., Eds., University Park, 1981, which is hereby incorporated by reference in its entirety. Immunoassays may be performed in which a solid phase support is contacted with the test sample. Any proteins present in the test sample bind the solid phase support and can be detected by a specific, detectable antibody preparations, examples of such techniques include the dot blot, Western blot and other similar assays variants. Western blot techniques, are described, for example, in Sambrook, J. et al., (1989) Molecular Cloning: A Laboratory Manual, Cold Spring Harbor Laboratory Press, Cold Spring Harbor, N.Y.

Other, more complex, immunoassays include, for example, "sandwich" assays for the detection of a protein in which a first anti-protein antibody bound to a solid phase support is contacted with the test sample. After a suitable incubation period, the solid phase support is washed to remove unbound protein. A second, different anti-protein antibody is then added which is specific for a portion of the specific protein not recognized by the first antibody. In this case, the secondary antibody is preferably detectably-labeled with the luminescent moiety. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds specifically to the second antibody (but not the first antibody) is added to the system.

The results from this type of assay can be a simple yes/no answer or can be expressed as, for example, (a) one or more of "excellent", "good", "satisfactory", "unsatisfactory"; and/or "poor"; (b) one or more of "very high", "high", "average", "low", and/or "very low"; or (c) one or more of "+++++", "++++", "+++", "++", "+", "+/−", and/or "−". In this aspect, the assay is a qualitative assay. Alternatively, the assay results can be quantitative by comparing the amount of detectable antibody with that obtained in a control. Examples of such assays are described in Wide et al., Radioimmune Assay Method, Kirkham, Ed., E. & S. Livingstone, Edinburgh, 1970, pp. 199-206, which is incorporated by reference in its entirety.

Other types of immunometric assays include "simultaneous," "reverse" assays."

The first component of the immunometric assay may be added to nitrocellulose or other solid phase support which is capable of immobilizing proteins. "Solid phase support" or "support" as used herein refers to any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead (e.g., agarose, sepharose, or magnetic beads), or cylindrical, as in the inside surface of a test tube or the external surface of a rod. One of skill in the art would know many other suitable "solid phase supports" for binding proteins. For example, a preferred solid phase support is a 96 or 386-well microtiter plate.

Detection of the protein-specific antibody, an antigen-binding-fragment thereof, or a derivative thereof can be accomplished using a fluorometer if, for example, one or both of the fluorescent sensitizer moieties are to be detected, or using a luminometer, if the emissions from the luminescent moiety is to be detected. Positive and negative controls may be performed in which known amounts of one or more antigens are added to assays being performed in parallel with the test assay. One skilled in the art would have the necessary knowledge to perform the appropriate controls.

Alternatively, in some embodiments, the probe moiety can be a ligand for a cellular receptor. Examples of such ligands that can be conjugated to a luminescent moiety described herein, and useful for the method include, but are not limited to: cytokines (e.g., Interferons (e.g., IFN-gamma), IL-2 subfamily cytokines, IL-10 subfamily cytokines, IL-1 subfamily cytokines, IL-17 subfamily cytokines, and Tumor Necrosis Factor); growth factors (PDGF, EGF, TGF-alpha, FGF, NGF, Erythropoetin, TGF-beta, IGF-I, IGF-II, G-CSF, GM-SCF, thrombopoietin, and myostatin); and viruses or viral proteins (e.g., viral surface or coat proteins, e.g., gp160 or p24 of HIV-1). In other embodiments, the ligand can also be a small molecule (e.g., an androgen (e.g., testosterone for binding to the androgen receptor), estrogen, progesterone, glucocorticoids, or corticosteroids). Where the small molecule is an orphan compound (i.e., a compound with a known function but no identified cellular target), the methods can be used to identify the cellular target of the orphan compound (e.g., the enzyme target of the compound).

Suitable detection methods for ligand-based luminescent conjugates are well known to those in the art and include some of the methods described above. Briefly, a ligand conjugate can be added to a sample for an amount of time sufficient to allow for the binding of the ligand to its cognate receptor, followed by detecting the emissions from the luminescent moiety or fluorescent emissions from one or both fluorescent sensitizer moieties. Optionally, the ligand can be unlabeled and a detectably-labeled antibody (such as one described above) can be used to detect the presence of the ligand.

In some embodiments, the probe moiety is a nucleic acid (e.g., RNA or DNA). Suitable uses for luminescently conjugated nucleic acids include, for example, mRNA sequence-based methods of detection including, but are not limited to, Reverse-transcriptase-polymerase chain reaction (RT-PCR) technology, branched oligonucleotide technology, Northern and Southern blot technology, in situ hybridization technology (e.g., fluorescence in-situ hybridization (FISH)) and oligonucleotide hybridization technology.

One method of detecting a particular mRNA transcript in genetic material derived from a sample (e.g., human cancer patient sample) uses branched chain oligonucleotide hybridization analysis. Branched-chain oligonucleotide hybridization may be performed as described in U.S. Pat. No. 5,597,909, U.S. Pat. No. 5,437,977 and U.S. Pat. No. 5,430,138.

In another embodiment, detecting an mRNA transcript in a sample using a luminescently-conjugated-nucleic acid probe described herein uses Northern Blot analysis. The techniques for performing Northern blot analyses are well known by those having ordinary skill in the art and are described in Sambrook, J. et al., (1989) Molecular Cloning: A Laboratory Manual, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

Another method of detecting the presence of a given mRNA transcript, embraced by the invention, uses by oligonucleotide hybridization technology. Oligonucleotide hybridization technology is well known to those having ordinary skill in the art (and described in greater detail below). Briefly, detectable probes which contain a specific nucleotide sequence that will hybridize to nucleotide sequence of the mRNA transcript. In one embodiment, RNA or cDNA made from RNA from a sample is fixed to, for example, filter paper. The probes are then added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences. Probes useful in such methods include oligonucleotides at least 18 nucleotides of complementary DNA and may be as large as a complete complementary sequence to the target mRNA transcript. In some preferred embodiments the probes of the invention are 30-200 nucleotides, preferably 40-100 nucleotides. The probes preferably contain a sequence that is unique with respect to the target mRNA sequence. Hybridization conditions can be routinely optimized to minimize background signal by non-fully complementary hybridization. In some preferred embodiments, the probes are full length clones. Probes are at least 15 nucleotides, preferably 30-200, more preferably 40-100 nucleotide fragments and can be the entire mRNA transcript.

Oligonucleotide hybridization techniques are useful for detecting an mRNA transcript in homogenized tissue samples and cells in body fluid samples. Furthermore, multiple methods of detection (including both described herein and other suitable detection techniques) can be combined in a given analysis. For example, techniques such as immunohistochemistry assays may be performed to determine whether one or more polypeptide products are present in cells in a sample as well as using, for example, RT-PCR or northern blot analysis to detect the presence of mRNA that encodes the polypeptide.

Additional embodiments of the luminescently-labeled nucleic acids are described in detail below under the section "Use of the Conjugates as Nucleic Acid Probes."

In Vivo Methods of Detection

This invention also features compositions and in vivo methods for detecting a target with a probe (e.g., a target in or on a subject). The methods include the steps of: delivering to a subject a luminescent probe composition comprising a targeting-probe moiety having an affinity for a target, the targeting-probe moiety covalently conjugated to a luminescent chelate composition comprising: (i) a first sensitizer moiety; (ii) a chelating moiety covalently joined, optionally through a first linker, to the first sensitizer; and (iii) a second sensitizer moiety covalently joined, optionally through a second linker, to the chelating moiety of (ii); wherein, the first and second sensitizer moiety, independently, have the Formula (I) or the Formula (II), wherein Formula (I) is:

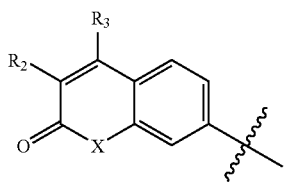

and wherein:
X is CH—$R_1$, O, S, or N—$R_1$;
$R_1$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_2$ is H; $NH_2$; carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene moieties are optionally further substituted with from 1-3 halo atoms; and
wherein the

at position 7 of the phenyl ring indicates the site of covalent attachment, optionally through a linker, of the sensitizer moiety to the chelating moiety; and
wherein Formula (II) is:

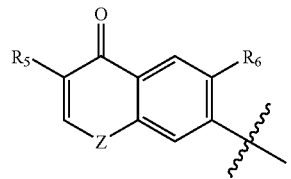

and wherein:
Z is CH—$R_4$, O, S, or N—$R_4$;
$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms;

$R_5$ is carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;

$R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and wherein the

at position 7 of the phenyl ring indicates the site of covalent attachment, optionally through a linker, of the sensitizer moiety to the chelating moiety; and wherein the chelating moiety is selected from the group consisting of: EDTA, DTPA, TTHA, DOTA, TAGA, DOTP, DTPA-BMA, DO2P, and HP-DO3A; and wherein one of the sensitizer moieties is covalently linked at the $R_2$ or $R_5$ position, optionally through a third linker moiety, to a conjugating group; and wherein the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV); and detecting a signal produced from the luminescent probe composition.

Methods of detection can be any of those described herein (see "Detecting Luminescence and/or Fluorescence of the Compositions"), and be performed using, for example, a fluoriscope, a luminoscope, nuclear magnetic resonance imaging (MRI), or computed tomography (CT scan).

The methods can be useful in in vivo diagnostics of biomarkers including, for example, tumor antigens (e.g., MAGE-1, MAGE-3, MUC1, FAP-α, Tenascin, Epidermal Growth Factor Receptor (EGFR), p185$^{HER2}$, Her-2/Neu, or CA-125), biomarkers of cardiac disease (e.g., CK, CK-MB, myoglobin, cardiac troponin, LDH, AST, Hs-CRP, or BNP), or biomarkers of neurologic disorders (e.g., tau, transthyretin, or alpha-synuclein). Biomarkers include both nucleic acids (e.g., mRNA) or protein (e.g., expression of a protein by a cell). When the methods are used at one time point (i.e., for one independent measurement), the methods can be used to detect the presence of a disease (e.g., a cancer, a cardiac disease, a microbial infection, or a neurologic disorder). Alternatively, when the methods are repeated for a given subject over time (i.e., biomarker detection in the same subject at various points in time), the methods can be used to detect or quantify the progression of a disease state in a subject (e.g., detect the worsening or amelioration of the disease based on, for example, an increase or decrease in the biomarkers of the diseases). For example, when more MAGE-1 is detected in a melanoma at a second time point as compared to the amount of MAGE-1 detected on the melanoma initially, this could be an indication that the melanoma is progressing.

The methods can also be useful in identifying or imaging in a subject the location of a given target to which the probe is drawn. For example, where the target of the probe is an antigen expressed on or in a tumor cell, or is a bona fide tumor antigen, the methods can be used to locate a tumor in the subject (e.g., find, detect, or identify a metastatic tumor cell or colony of cells). The methods can also be useful in detecting blood clots or thromboses in a subject, by for example, venographies.

Other uses for the method can be cardiac stress tests, lung scans, pulmonary angiograms, and spiral (helical) computerized tomography (CD scans.

The subject can be any subject described herein.

All of the conjugated probes described herein can be used for the in vivo methods. For example, luminescent probe compositions useful in the method include compositions where the probe is, for example, an antibody, ligand, small molecule, or nucleic acid. Suitable probes will vary upon the type of target molecule to which the probe is drawn.

Where the probe moiety is an antibody, it may be useful (e.g., when the intended subject is a human) to partially humanize or fully humanize the antibody probe. The conjugated antibody or antigen binding fragment of the invention may be modified in such a way as to make it more compatible for in vitro or in vivo use. EP 239 400 (Winter et al.) describes altering antibodies by substitution (within a given variable region) of their CDRs for one species with those from another. CDR-substituted antibodies can be less likely to elicit an immune response in humans compared to true chimeric antibodies because the CDR-substituted antibodies contain considerably less non-human components. See Riechmann et al., 1988, Nature 332, 323-327; Verhoeyen et al., 1988, Science 239, 1534-1536. Typically, CDRs of a murine antibody are substituted into the corresponding regions in a human antibody by using recombinant nucleic acid technology to produce sequences encoding the desired substituted antibody. Human constant region gene segments of the desired isotype (e.g., gamma I for CH and kappa for CL) can be added and the humanized heavy and light chain genes can be co-expressed in mammalian cells to produce soluble humanized antibody.

WO 90/07861 describes a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271 use, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from x-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more (preferably at least five, ten, twelve, or all) of the following positions: (in the framework of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the framework of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

Fully human monoclonal antibodies that bind to a V2-CND polypeptide can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798, 230. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; US 2003-0232333).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with a V2-CND polypeptide.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., heavy chain (HC) CDR1, HC CDR2, HC CDR3, light chain (LC) CDR1, LC CDR2, and LC CDR3, can be human. Each of the light chain CDRs can be human. HC CDR3 can be human. One or more of the framework regions (FR) can be human, e.g., FR1, FR2, FR3, and FR4 of the HC or LC. In some embodiments, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762. In some cases, humanized immunoglobulins can include a non-human amino acid at one or more framework amino acid positions.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids) are similarly encoded by a variable region gene (about 116 amino acids) and one of the other aforementioned constant region genes, e.g., gamma (encoding about 330 amino acids).

The term "antigen-binding fragment" of a full length antibody refers to one or more fragments of a full-length antibody that retain the ability to specifically bind to a target of interest (i.e., GFRalpha3). Examples of binding fragments encompassed within the term "antigen-binding fragment" of a full length antibody include: (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

Pharmaceutical Compositions and Methods of Delivery of Compositions

The present invention also provides for pharmaceutical compositions containing any of the compositions described herein, or a pharmaceutically acceptable salt thereof, the composition covalently joined to a probe, together with a pharmaceutically acceptable carrier, diluent, or excipient therefor.

Any of the chemical compositions described herein can be incorporated into pharmaceutical compositions. Such pharmaceutical compositions typically include the chemical compositions and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A chemical composition of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds can also be incorporated into the pharmaceutical compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL3 (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating any of the chemical compositions described herein in the required amount in an appropriate solvent with one or a combination of ingredients enumerated above, as required, followed by filtered sterilization. Generally, dispersions are prepared by incorporating the chemical composition into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral pharmaceutical compositions generally include an inert diluent or an edible carrier. For the purpose of oral therapeutic administration, the chemical composition can be incorporated with excipients and used in the form of tablets, troches, or capsules, e.g., gelatin capsules. Oral pharmaceutical compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets contain from 1% to 95% (w/w) of the chemical composition. In certain embodiments, the chemical composition ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the chemical composition with encapsulating material as a carrier providing a capsule in which the chemical composition with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the chemical composition in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the chemical compositions are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The chemical compositions can also be prepared in the form of suppositories (e.g., with conventional suppository bases such as cocoa butter and other glycerides) or retention enemas for rectal delivery.

In one embodiment, the chemical compositions are prepared with carriers that will protect the chemical composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral pharmaceutical compositions in dosage unit form for ease of administration and uniformity of dosage. Dosage unit form as used herein refers to physically discrete units suited as unitary dosages for the subject to be treated; each unit containing a predetermined quantity of a chemical composition calculated to achieve the desired level of detection in association with the required pharmaceutical carrier. Dosage units can also be accompanied by instructions for use.

The dose administered to a subject, in the context of the present invention should be sufficient to achieve a desired level of detection in the subject over time. The dose will be determined by the efficacy of the particular chemical composition employed in detection, the accessibility of the particular target to which the probe is drawn, and the condition of the subject, as well as the body weight or surface area of the subject to be treated. The size of the dose also will be determined by the existence, nature, and extent of any adverse side effects that accompany the administration of a particular chemical composition in a particular subject.

For administration, chemical compositions of the present invention can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

The pharmaceutical compositions can be included in a container, pack, or dispenser together with instructions for administration.

Detecting Luminescence and/or Fluorescence of the Compositions

A variety of radiation sources and radiation wavelengths can be used to excite the luminescent compositions described herein. For example, lamps (e.g., high pressure, mercury, xenon, and quartz lamps) and lasers generating radiation having suitable wavelengths can be employed for exciting the luminescent compositions.

Methods of assessing the luminescence intensity of a composition described herein can be quantitative, semi-quantitative, or qualitative. Thus, for example, the emission intensity of a given composition can be determined as a discrete value. Such quantitative methods are well known to those of ordinary skill in the art, and methods are described in the following Examples. Such methods involve, for example, placing a sample into a spectrophotometer, luminometer, or fluorimeter cable of exciting one or both of the sensitizer moieties of the compositions described herein, and detecting (e.g., determining, or measuring) the fluorescent emission from one or both of the sensitizer moieties, and/or detecting the luminescent emissions from the luminescent moiety (e.g., the metal chelate, e.g., the lanthanide). Where the detection occurs in vivo (e.g., in the whole animal), the detection can be performed using, for example, a fluoroscope, a luminoscope, nuclear magnetic resonance imaging (MRI), or computed tomography (CT scan). The excitation light can be constant, or preferably, the excitation light can be pulsed. Excitation of the one or more sensitizer moieties can occur at a range of 400-700 nm and is dependent on the absorption maxima of a particular sensitizer. A luminescent chelate described herein containing a lanthanide, Tb3+ for example, can be excited at wavelengths of between 150 and 750 nm, usually between 200 and 650 nm, more usually between 250 and 550 nm, and most often between 300 and 450 nm. Generally, detected emissions are at least 50 nm, usually at least 100 nm, more usually at least 150 nm greater than the incident light. For example, preferred detected emissions for terbium and europium are 492 and 546 nm and 617 and 695 nm, respectively. One of ordinary skill in the art would know how to perform routine experimentation to determine optimal excitation wavelengths for the luminescent compositions depending on the particular sensitizer moiety. Examples of fluorescent emissions and excitation spectra for numerous fluorophore molecules can be found at, e.g., http://probes.invitrogen.com/servlets/spectra/ (Invitrogen, Carlsbad, Calif., USA).

It is understood that for any of the methods described herein, detection can involve detecting luminescence emissions of the excited luminescent chelate moiety and/or the fluorescence emissions of one or both sensitizer moieties of the luminescent compositions. Fluorescence emissions of the sensitizers (i.e., the fluorophores) can range from 400-700, dependent on a particular sensitizer.

Conjugation of the Compositions to Macromolecular Probes

Provided herein are conjugates of any of the chemical compositions described herein and a probe moiety. The macromolecular conjugates of the luminescent compositions described herein are useful for a variety of methods including: immunochemistry, fluorescence in situ hybridization (FISH), cell tracing, receptor labeling and fluorescent analog cytochemistry. In these applications, the stability of the chemical bond between the luminescent composition and macromolecule (i.e., the probe) is particularly important because the conjugate can typically be stored and/or used repeatedly over a relatively long period of time. Moreover, the conjugates can often be subjected to rigorous incubation, hybridization and washing steps that demand a strong composition-macromolecule linkage.

The preferred conjugate usually has a high luminescence and/or fluorescence yield (or, in the case of a haptenylated conjugate, a suitable degree of labeling) yet retains the critical parameters of the unlabeled biomolecule, such as solubility, selective binding to a receptor (e.g., where the probe is a ligand to a particular cognate receptor), a target antigen (e.g., where the probe is an antibody) or nucleic acid (e.g., where the probe is a complementary nucleic acid to the target nucleic acid), activation or inhibition of a particular enzyme or the ability to incorporate into a biological membrane. Following conjugation, it is very important to remove as much unconjugated labeling reagent as possible, usually by gel filtration, dialysis, macromolecule precipitation and resolubilization, HPLC or a combination of these techniques. The presence of free dye, particularly if it remains chemically reactive, can greatly complicate subsequent experiments with the luminescent macromolecular conjugates.

Methods for conjugating any of the compositions described herein with a polypeptide are well known to those of ordinary skill in the art. For example, proteins may be labeled in a variety of ways to allow efficient detection or purification. The labeling methods make use of one or more common functional groups on the surface of protein molecules. Primary amine groups ($-NH_2$), present at the N-terminus of each polypeptide chain and the side chain of lysine residues can be conjugated to a composition. Alternatively, sulfhydryl groups ($-SH$), present on cysteine residues can be made available by treating disulfide bonds with a reducing agent or by modifying lysine residues with a reagent such as SATA. Particularly useful for conjugation to antibodies, carbohydrate groups, usually present in the Fc region of polyclonal antibodies, may be oxidized to create active aldehydes ($-CHO$) for coupling (see, for example, Qu et al. (1998) J. Immunol. Meth. 213:131-144. In some embodiments, the chemical compositions described herein are covalently joined to "conjugating moieties." These conjugating moieties are molecules that contain chemically reactive groups that, when reacted with a probe moiety, are capable of joining the chemical composition and the probe moiety. Examples of such conjugating moieties include, but are not limited to, an amine reactive moiety having the chemical formula $-N=C=S$ or a thiol-reactive moiety having the chemical formula $-CO-CH_2-Br$.

Additional methods of conjugation of a composition to a macromolecule or probe include, e.g., succinimidyl esters, carbonyl azides, sulfonyl chlorides and aldehydes.

Succinimidyl esters are excellent reagents for amine modification because the amide bonds they form are as stable as peptide bonds. These reagents are generally stable during storage if well desiccated, and show good reactivity with aliphatic amines and very low reactivity with aromatic amines, alcohols, phenols (including tyrosine) and histidine. Succinimidyl esters will also react with thiols in organic solvents to form thioesters. If formed in a protein, a thioester may transfer the acyl moiety to a nearby amine. Succinimidyl ester hydrolysis can compete with conjugation, but this side reaction is usually slow below pH 9.

Carbonyl azides are active esters that can react with amines to yield amides; however, a more common application of carbonyl azides is thermal rearrangement to a labile isocyanate (which can react with both aliphatic and aromatic amines to form ureas) for derivatizing alcohols and phenols.

Sulfonyl chlorides, including the dansyl, pyrene, Lissamine rhodamine B and Texas Red derivatives, are highly reactive. These reagents are quite unstable in water, especially at the higher pH required for reaction with aliphatic amines. Protein modification, for example, with this reagent is best done at low temperature. Once conjugated, however, the sulfonamides that are formed are extremely stable; they even survive complete protein hydrolysis (for example, dansyl end-group analysis. Sulfonyl chlorides can also react with phenols (including tyrosine), aliphatic alcohols (including polysaccharides), thiols (such as cysteine) and imidazoles (such as histidine), but these reactions are not common in proteins or in aqueous solution. Sulfonyl chloride conjugates of thiols and imidazoles are generally unstable, and conjugates of aliphatic alcohols are subject to nucleophilic displacement.

Aldehydes react with amines to form Schiff bases. Notable aldehyde-containing reagents described include o-phthaldialdehyde (OPA), naphthalenedicarboxaldehyde (NDA) and the 3-acylquinolinecarboxaldehyde (ATTO-TAG) reagents CBQCA and FQ. In addition, certain arylating reagents such as NBD chloride, NBD fluoride and dichlorotriazines react with both amines and thiols, forming bonds with amines that are particularly stable.

It is understood that any methods for conjugating a composition to a probe moiety will vary depending on, for example, the composition to be conjugated and the particular probe moiety that the chemical composition is conjugated to.

Use of the Conjugates as Nucleic Acid Probes

Conjugates of the luminescent compositions and nucleic acids (e.g., hybridization probes) of the invention can be made from DNA, RNA, or some combination of the two. The probes can include modified nucleotides. The links between nucleosides in the probes may include bonds other than phosphodiester bonds.

In one embodiment, the luminescent hybridization probes are "molecular beacon"-type probes that are interactively labeled, hairpin forming oligonucleotides comprising a stem-and-loop structure. The loop contains a probe sequence complementary to the probe's target. Nucleotide sequences ("arms") flank the probe sequence and a sequence in one arm is complementary to a sequence in the other arm. When the probe is not hybridized to a target, the arms hybridize to one another and form a stem hybrid, which is sometimes referred to as a stem-duplex. This is the closed conformation. When the probe hybridizes to its target sequence, the longer and stronger probe-target hybrid overcomes the stem hybrid and separates the arm sequences. This is the open conformation. In the open conformation an arm can also hybridize to the target. For some molecular beacon probes, only perfectly complementary strands are targets that cause this change under assay conditions; for other embodiments the probe will open despite the presence of one or a few internal mismatches with the target. The molecular beacon probes described herein have a luminescent composition (e.g., any of the luminescent compositions of matter described herein) attached (e.g., covalently conjugated) to one arm and a quencher (for definition, see below) attached to the other arm. When the arms form the stem, the quencher is very close to the fluorophore/luminophore and effectively quenches or suppresses its fluorescence, rendering it dark.

As used herein, a "quencher" refers to a molecule or moiety that, when placed very close to an excited fluorophore, causes there to be very little or no fluorescence. Similarly a quencher when placed close to an excited luminophore causes there to be little or no luminescence emitted from the luminophore. Where the quencher moiety quenches both a fluorophore and a luminophore (e.g., a fluorophore and luminophore in a luminescence resonance energy transfer (LRET) relationship, see below), the quencher is a double quencher or "doubly quenches." Suitable quenchers described in the art include DABCYL and variants thereof, such as DABSYL, DABM1, and Methyl Red. Some fluorophores can also be quenchers, for examples, fluorophores that touch certain other fluorophores. Preferred quenchers are DABCYL, malachite green, or fluorophores that do not fluoresce in the detection range when the probe is in the open conformation.

The oligonucleotide sequences of molecular beacon probes modified according to this invention may be DNA, RNA, peptide nucleic acid (PNA) or combinations thereof. Modified nucleotides may be included, for example nitropyrole-based nucleotides or 2'-O-methylribonucleotides. Modified linkages also may be included, for example phosphorothioates. Modified nucleotides and modified linkages may also be incorporated in wavelength-shifting primers according to this invention, subject, as will be recognized, to the requirement that one arm be able to serve a primer for a nucleic acid polymerase.

For probes according to this invention, the length of the loop sequence that is target complementary, the length of the stem hybrid and the relation of the two is designed according to the assay conditions for which the probe is to be utilized. Lengths of target-complement sequence and stem hybrid for particular assay conditions can be estimated by known means, tried and adjusted, if necessary. Typical probe sequences for use in PCR assays are in the range of 16 to 25 nucleotides. Typical stem lengths are in the range of 3 to 8, more commonly 4 to 7 nucleotides. The strength of the stem hybrid is adjusted by routine experimentation to achieve proper functioning. In addition to length, the strength of the stem hybrid can be adjusted by altering the G-C content and insertion of destabilizing mismatches, as will be appreciated. One arm can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, as well as being free-floating.

Hairpin-forming probes according to this invention may be utilized in detection assays. They may also be used as detectors in amplifications assays, and may be added prior to amplification, in which case quantitative results as to the initial concentration of amplifiable target may be obtained. Amplification reactions include the polymerase chain reaction (PCR), strand displacement amplification (SDA), nucleic acid sequence based amplification (NASBA), transcription mediated amplification (TMA), the ligase chain reaction (LCR), rolling circle amplification, and RNA-directed RNA amplification catalyzed by an enzyme such as Q-beta replicase. Multiple probes for multiple targets may be used in a single reaction tube or other container for multiplex assays.

Hairpin-forming primers are used in those of the amplification reactions identified above that include one or more primers. They may be modified according to the present invention to have an arm sequence that binds to a nucleic acid target, such that the hairpin-containing primer can be extended by incubation with a nucleic acid polymerase. The loop portion may, but need not be, complementary to the original target strand. Hairpin-containing primers have a stem labeled with a fluorophore on one arm and a quencher on the other arm, similarly to molecular beacon detection probes. Embodiments of the instant invention will be described primarily in connection with molecular beacon detection probes. Those of skill in the art will understand that the concepts and teachings apply to hairpin primers as well, and will understand how to apply the concepts and particular teachings to hairpin-containing primers.

Further description of uses for the luminescent compositions as part of molecular beacons and the like, including quenchers and additional fluorophores, can be found in, e.g., U.S. Pat. No. 6,037,130; U.S. patent application Ser. No. 08/439,619 and Ser. No. 08/990,176, which are incorporated herein by reference in their entirety.

Assays that utilize the nucleic acid probes (e.g., conjugates of any of the compositions herein with nucleic acid) of this invention begin simply by addition of the probes to the material of interest under conditions that are conducive to hybridization. The methods of processing the samples and monitoring the fluorescence signal may vary with the nature of the samples. Tissues may be disrupted mechanically or by incubation with chaotropic salts. Most disrupted tissues may be used directly in the assays. Some tissues, however, contain naturally fluorescent materials that may interfere with the detection of signal. In such cases, the nucleic acids may be isolated from the fluorescent materials either before or after hybridization. The fluorescence of opened probes can be monitored by fluorometers. The luminescence of opened probes can be monitored by luminometer.

The conjugates of the composition and nucleic acids (e.g., DNA, e.g., probes) described herein are useful, for example, in field tests for certain infectious diseases. For example, a test for malaria or HIV-1 may begin by addition of guanidine thiocyanate to a sample of blood to lyse the cells, detoxify the cells and denature the constituents. A large excess of a probe (relative to the expected maximal target concentration) which is complementary to, for example, a ribosomal RNA of the malarial parasite may then be added, and hybridization allowed to proceed. Luminescence or fluorescence of open probes may be monitored either visually or with help of a luminometer or fluorometer. Detection of a positive luminescent and/or fluorescent signal indicates an infection by the malarial parasite or HIV-1 virus.

Any of the probes described herein can be used to locate particular nucleic acid fragments in a gel or other medium, for example where information on the size of a specific nucleic acid is desired. The nucleic acids in the sample can first be fractionated by gel electrophoresis and then the gel itself bathed in a solution containing the probes. The location in the gel where the target nucleic acid migrates will be detectable by the characteristic signal as a result of hybridization.

Production of nucleic acids in synthesis reactions may be monitored by including appropriately designed probes in the reaction mixture and monitoring the level of signal, e.g., luminescence, in real-time. The probes should be designed to be complementary to a segment of the nucleic acid that is produced. Examples of such reactions are RNA synthesis by DNA-dependent RNA polymerases and by Q-beta replicase. Unimolecular probes are particularly useful in tracking a polymerase chain reaction, since they open and close with a speed faster than the speed of thermal cycles used in this reaction. An additional temperature in each cycle, which is 5-12 EC lower than the melting temperature of the stem of the probe, may be included as the detection temperature. In each cycle, the level of luminescence will indicate the amount of target DNA strand present. An excess of the probes, as an excess of PCR primers, in the reaction mixture should be used. The PCR may be asymmetric. Real-time monitoring of the correct products, as opposed to end-point detection, improves the precision and the dynamic range of the estimates of the target nucleic acid concentrations by polymerase chain reactions and obviates the need for post-amplification analysis.

The luminescent probes described herein can also be used for monitoring other nucleic acid amplification reactions, such as strand displacement amplification reactions and self-sustained sequence replication reactions. Useful probes are designed and used in a manner similar to the probes for polymerase chain reaction products.

Additional embodiments and examples of the use of such probes are described in U.S. application Ser. Nos. 08/152,006; 60/161,096; and 10/426,556, and U.S. Pat. Nos. 5,925,517; 6,150,097; 6,461,817; and 6,037,130, which are hereby incorporated by reference in their entirety.

Luminescence Resonance Energy Transfer and Assays

Any of the compositions or their conjugates can use, for example, Luminescence Resonance Energy Transfer (LRET) as a mechanism of signal generation. FRET can be used to measure the distances between two points that are labeled with fluorescent dyes and separated by approximately 10-75 angstroms. The technique is valuable because measurements can be made under physiological (or other) conditions with near-Angstrom resolution and with the exquisite sensitivity of fluorescence measurements. FRET relies on a distant-dependent transfer of energy from one fluorescent dye—the donor—to another absorbing or fluorescent dye—the acceptor. The donor and acceptor are site-specifically placed at the two points that one wishes to measure the distance between.

While lanthanides do not fluoresce, the use of any of the luminescent compositions (or conjugates thereof) described herein permits them to be efficiently excited. A non-fluorescent quantum transition of the lanthandide can then effect a non-radiative energy transfer to a suitable and appropriately distanced acceptor. To effect transfer, an acceptor absorption must overlap a lanthanide emission. The chelate—acceptor pair is selected for optimal overlap: for longer distance measurements, greater overlap is preferred. Since the lanthanides have lifetimes on the order of a millisecond, the signal-to-noise ratio of sensitized emission of the acceptor in LRET is improved by emission detection through time resolution (pulse delay) or phase modulation. Energy transfer can be detected by donor quenching or, preferably acceptor luminescence.

By using luminescent lanthanide chelators as donors (instead of conventional dyes), and conventional fluorescent dyes as acceptors, we have improved the signal to background of LRET by approximately 100-fold. This improvement allows measurements beyond 100 angstroms, a distance currently unmeasurable using small, conventional fluorescent dyes. This distance regime is important in many biological problems. Using lanthanide chelators as donors also makes distance measurements more accurate, because the chelators minimize the uncertainty in the orientation-dependence of energy transfer.

LRET is particularly useful to obtain structural and kinetic information about macromolecules in solution, in real time. For example, double-end labeled oligonucleotides provide detectable LRET signaling when bound by nucleic acid binding proteins, e.g. transcription factors. Accordingly, the methods are used to screen for potential therapeutics that alter the structure or interactions of biomolecules; for example, antiviral agents are screened for the ability to alter vital transcription factor-induced alterations in nucleic acid conformation.

The general LRET-based method of detecting the distance between a first position and a second position in a portion of a sample involves: exposing a sample portion comprising the donor lanthanide-chelate complex located at the first position and the acceptor located at the second position to light at a first wavelength capable of inducing a first electronic transition in the donor. The spectral overlap of the donor emission and acceptor absorption is sufficient to enable energy transfer from the donor to the acceptor as measured by detectable quenching of donor luminescence intensity or lifetime or detectable increase in acceptor luminescence intensity or lifetime. Then the intensity of a first emission of light from the sample portion at a second wavelength is detected wherein the second wavelength is longer than the first wavelength and results from a second electronic transition in the donor, wherein the intensity of the first emission of light correlates with the distance between the first and second positions. In other words, the closer the positions, the greater the energy transfer and the greater the donor quenching. Alternatively, one can detect the intensity of a second emission of light from sample portion at a third wavelength, wherein the third wavelength is longer than the first wavelength and results from an electronic transition in the acceptor, wherein the intensity of the second emission of light inversely correlates with the distance between the first and second positions of the sample portion. In other words, the closer the positions, the greater the energy transfer and the greater the acceptor luminescence.

This general method has broad application whenever the static or dynamic distance between to positions, e.g. two atoms or molecules, is of interest. In one specific embodiment, the method is used to monitor the status of a polymerase chain reaction. Here, the sample portion comprises a target nucleic acid strand comprising a first strand portion and a diagnostic nucleic acid strand labeled proximal to one end with the acceptor and proximal to the other end with the donor (i.e. comprising a first atom covalently joined to the donor and a second atom covalently joined to the acceptor, the first and second atoms being separated by a second strand portion). The first and second strand portions are sufficiently complementary to hybridize under annealing conditions, and the second strand portion is of sufficient length to provide a detectable difference in the aggregate energy transfer from the donor to the acceptor when the first and second strand portions are hybridized as compared with the aggregate energy transfer from the donor to the acceptor when the first and second strand portions are not hybridized. The detectable difference is measured as at least one of a detectable quenching of donor luminescence or detectable increase in acceptor luminescence, and the distance between the first and second atoms indicates whether the nucleic acid strands have hybridized. Thus, as the reaction proceeds, the stepwise increase in the mount of target nucleic acid is reflected in a stepwise decrease in energy transfer.

Detection or imaging methods using LRET or FRET are useful for such varied applications as detection of epitope mapping, peptides association in membranes, lipid order in vesicles, membrane organization, lipid distribution, protein folding kinetics, transport systems, in vivo protein-protein interactions, protein subunit exchanges, DNA-protein interactions, tRNA-ribosomes, DNA triple helixes, and nucleic acid hybridization.

In general, the compositions and conjugates thereof described herein can be used to detect and/or quantify a target material of interest containing, or derivatized to contain, a target sequence. The target-sequence-containing target material is incubated with luminescent conjugates described herein for a time period sufficient to allow binding to and/or labeling of the target material. FRET from the conjugate is detected, thereby detecting the target material. The target material can be detected in any material, including, but not limited to, cuvettes, microtiter plates, capillaries, flow cells, test tubes, gels, blots, and biological samples. In some embodiments, the target material can be detected in the body of a subject.

A FRET assay can also be used to monitor a reaction between analytes. For example, a kinase assay. Such methods are described in, for example, Von Ahsen et al. (2006) J Biomol. Screen; Green et al. (2005) BMC Chem. Biol. 5:1; and Mang et al. (2005) Anal Biochem. 343(10):76-83.

The reaction can also be, for example, a protein folding event, a cleavage event, a protein self-association event, or rates thereof. The method can be an immunoassay, a DNA-protein binding assay, a protein-protein assay, a protein conformational assay, and rate studies thereof, many of which are described above.

Additional description of LRET and FRET and methods of use can be found in, for example, U.S. Pat. No. 5,622,821; and Selvin et al. (2002) Ann. Rev. Biophys. Biomol. Structure 31:275-302, both of which are incorporated herein by reference in their entirety.

The following examples are meant to illustrate, not limit, the scope of the invention.

EXAMPLES

Example 1

The Synthesis of 4-quinolone Derivatives

Figure 2:
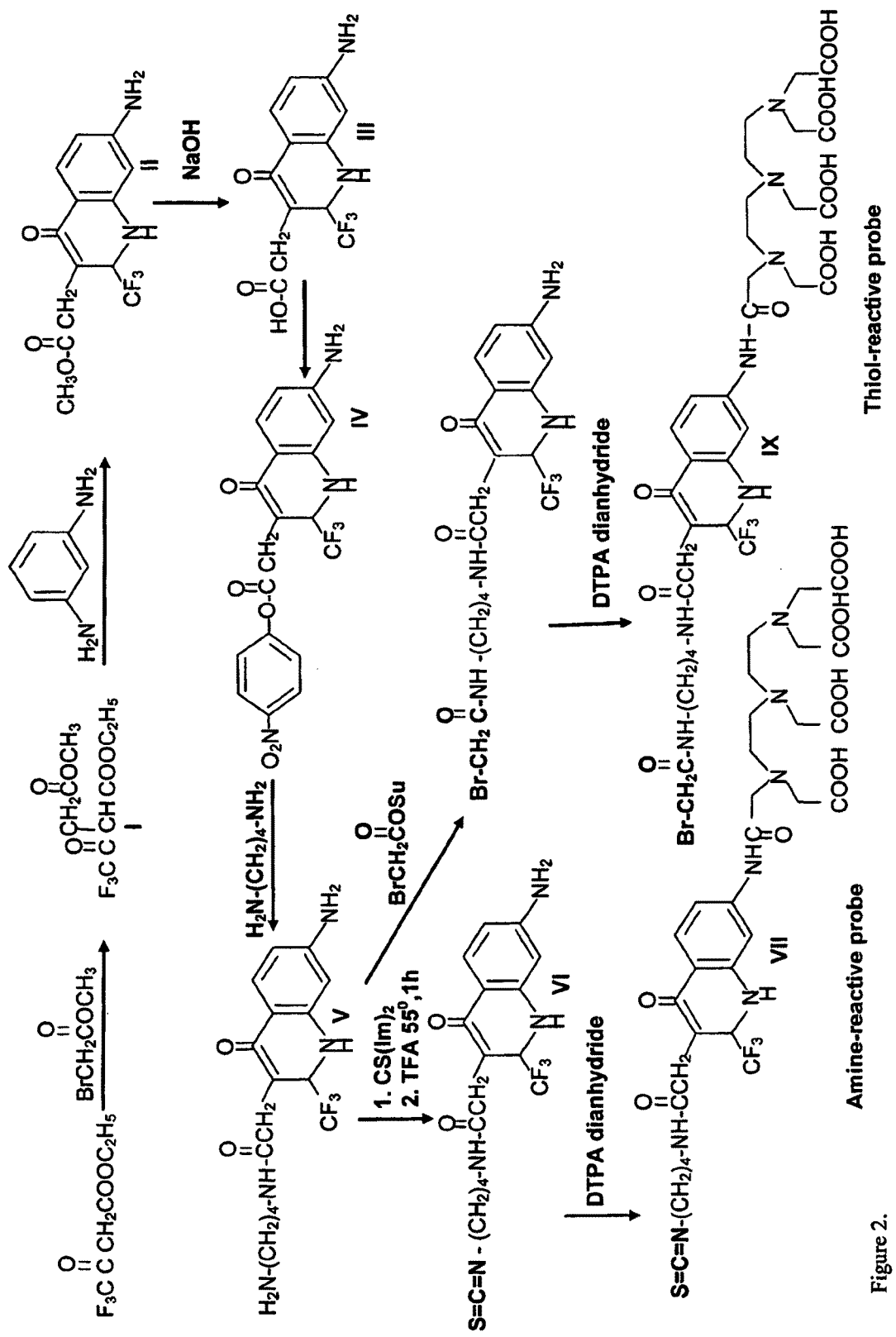
FIG. 2 is a depiction of a synthetic route for making 4-quinolone luminescent probes.

For the synthesis of Compound I of FIG. 2, 2.2 mL (15 mmol) of trifluoroacetoacetate and 0.6 g (15 mmol) of NaOH powder were mixed in 7 mL of dimethyl formamide and stirred at 40° C. until dissolved. To this mixture, 1.5 mL of bromoacetoacetate was added and the solution was incubated for 2 hours at 70° C. until the NaBr (sodium bromide) stopped precipitating. The mixture was diluted with 20 ml of water and extracted with ether. The organic layer was collected and evaporated in vacuo first at 30° C. and then at 70° C. for 30 minutes. Compound II of FIG. 2 was synthesized as follows: 1.0 g of 1,3-phenylenediamine was mixed with an equimolar amount of Compound I (FIG. 2) in 2 mL of DMSO and incubated at 50° C. for 18-20 hours. The main fluorescent product, with $R_f$=0.9 (Thin Layer Chromatography (TLC) on silicagel in ethylacetate), was formed under these conditions. The mixture was diluted with water and extracted with ether. The organic phase was collected and the product purified by column chromatography on silicagel using the mixture of hexane/acetone 4:1 as eluent.

Compound III was synthesized using compound II (FIG. 2) dissolved in 4-5 ml of 0.5 M NaOH in 50% ethanol and kept at 50° C. for 2 hours. The mixture was acidified by 1 M citric acid and extracted by ether. Ether was removed by evaporation in vacuo. Compound III was dissolved in 3 ml of THF and supplemented with 140 mg of 4-nitrophenol and 0.5 g of dicyclohexylcarbodiimide (DCC). Following a 30 minute incubation, 3 mmol of 1,4-diaminobutane in 3 ml of methanol was added to the above mixture and incubated an additional 5 minutes. The mixture was diluted with 10 mL of water, acidified with 1 M citric acid to pH 3-4 and extracted with ether. The pH of aqueous layer was adjusted to 12-13 by 10 M NaOH and the product extracted by ethylacetate. The organic phase was evaporated in vacuo, the residue dissolved in 30 ml of the mixture ether/ethanol 7:1 and shaken with equal volume of water. The organic phase was collected and evaporated in vacuo, followed by additional evaporation with acetonitrile. The residue was washed by chloroform (3×2 ml) and discarded. Chloroform extracts were combined and evaporated in vacuo. These steps resulted in the production of Compound V of FIG. 2.

Compound VI of FIG. 2 was generated by dissolving 40 mg of compound V in 2 mL of chloroform, supplemented with 25 mg of thiocarbonyldiimidazole. Following a 5 minute incubation, 0.1 mL of methanol and 25 mL of trifloroacetic acid (TFA) were added and incubation continued for another 1.5 hours at 55° C. The mixture was consecutively extracted with 1 ml of 0.1 M citric acid and 1 mL of 1 M NaHCO$_3$. Chloroform was removed by evaporation and the residue washed a few times with acetonitrile. Acetonitrile fractions were combined and evaporated in vacuo.

Compound VII of FIG. 2 was generated by dissolving 20 mg compound VI in 0.5 mL of DMF containing 32 mg of DTPA dianhydride and 14 µl of TEA. After a 20 minute incubation at 55° C. the product was purified by TLC on 2 silicagel plates in acetonitrile/water 5:1 system. Compound VIII of FIG. 2 was generated by dissolving 40 mg of compound V in 2.5 mL of methanol and mixed with equimolar amount of N-hydroxysuccinimidylbromoacetate. The mixture was evaporated in vacuo, the residue dissolved in ethylacetate and extracted with water containing 10 mM NaOH. The organic phase was collected and evaporated in vacuo. The residue was washed by acetonitrile and discarded. Acetonitrile wash was evaporated to dryness. Finally, compound IX of FIG. 2 was synthesized from compound VIII at the conditions analogous to those for the synthesis of compound VII.

Example 2

The Synthesis of 2-quinolone Derivatives

Figure 3:
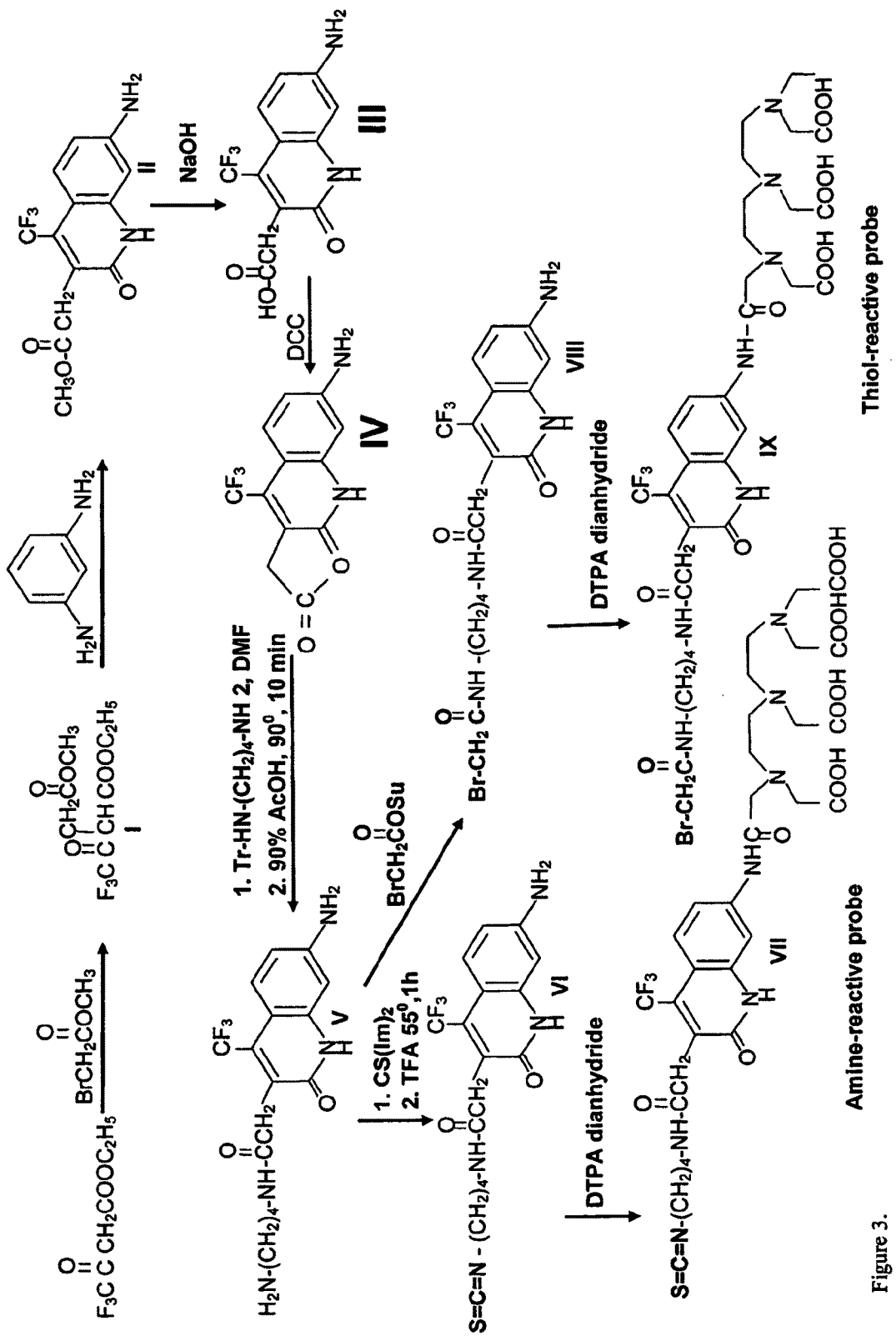
FIG. 3 is a depiction of a synthetic route for making 2-quinolone luminescent probes.

Compound II of FIG. 3 was obtained from compound I (see previous section, FIG. 2), however, a temperature of 110° C., instead of 50° C., and 4 h was used. The $R_f$ of Compound II of FIG. 3 was equal to 0.6 (TLC on silicagel in ethylacetate). The mixture was supplemented with 20 ml of water and extracted with ether (2×40 ml). The organic phase was collected and the product purified by column chromatography on silicagel using the mixture of hexane/acetone 3:1 as eluent. The fractions containing Compound II were collected, evaporated in vacuo and the residue suspended in 4-5 ml of chloroform. The solvent was removed by filtration and the residue dried under reduced pressure. Yield 260 mg. Compound III of FIG. 3 was obtained from compound III as described for corresponding product of FIG. 2.

Compound IV. 240 mg of compound III were suspended in 20 ml of THF and supplemented with 450 mg of DCC and agitated for 1 h at ambient temperature. TLC analysis in chloroform-ethanol system (2:1) detected single fluorescent product (Rf=0.8). The mixture was treated with 1.5 molar excess of monotrityl derivative of 1,4-diaminobutane for 20 min which resulted in complete conversion of compound IV to corresponding adduct (Rf=0.7 in ethylacetate-ethanol system, 10:1). The product was purified by column chromatography on silicagel using the same eluent. Yield 340 mg. Compound V was generated from this product by incubation in 90% acetic acid (5 ml) at 90° C. during 10 min. The solvent was removed in vacuo and the residue evaporated few more times with water to remove the traces of acetic acid. Finally the residue was dissolved in water, acidified to pH 3-3.5 and extracted with ether (2×20 ml). The water layer was collected, pH adjusted to 11.5-12 by NaOH and the product extracted by chloroform. The organic phase was collected, dried over sodium sulfate and the solvent removed in vacuo.

All other compounds were obtained as described for corresponding compounds in the previous section (see Example 1).

Example 3

Fluorescent Properties of 2 and 4-quinolone Derivatives

Figure 4:
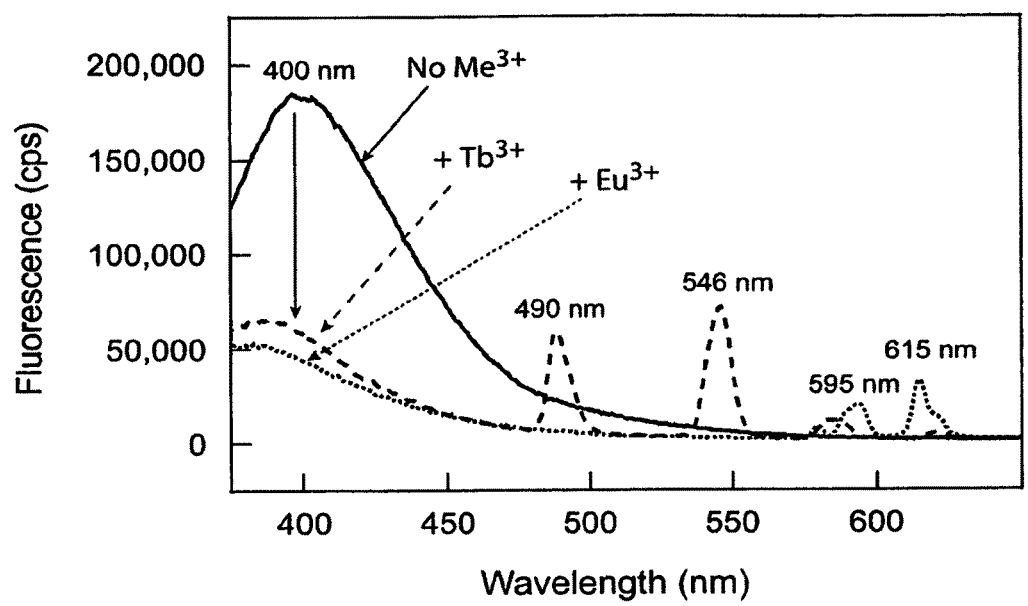
FIG. 4 is a depiction of emission spectra of the compound VII of FIG. 2 in metal free state as well as in the complex with $Eu^{3+}$ and $Tb^{3+}$.

FIG. 4 depicts fluorescence emission spectra for 4-quinolone compound VII of FIG. 2. The metal free compound possesses the broad emission spectrum centered at 400 nm. Addition of Eu$^{3+}$ or Tb$^{3+}$ results in coordination and efficient energy transfer to bound lanthanide, which is evidenced by decrease of the emission of antenna (at 400 nm) and appearance of sharply spiked peaks typical for lanthanide emission (at 490 nm, 546 nm, 580 nm, 622, nm for Tb$^{3+}$ and 570 nm, 595 nm, 615 nm for Eu$^{3+}$). Notably, time delayed fluorescence measurements of Lanthanide-coordinated probe show complete disappearance of the emission maximum at 400 nm, while lanthanide emission does not visibly decrease up to 50 µsec delay. This allows to achieve unusually high sensitivity of the probe detection, which was equal to 50 fM in our measurements.

Example 4

The Synthesis of Molecular Beacons Using 2 and 4-quinolone Derivatives

For preparation of molecular beacons we used 2'OMe RNA constructs containing common fluorescence quenchers, Black hole quencher (BHQ-2) and Dabsyl quencher (DAB) at 3' termini. Quinolone derivatives (compounds VII from FIGS. 2 and 3) were attached to these constructs at aminoalkyl function placed at 5' termini. Derivatization of the constructs was performed in 30 μl reaction mixture containing 0.1-0.5 mM polynucleotide material, 5 mM quinolone probe and 0.2 M sodium borate pH 10. After 3.5 h incubation at 55° C. the excess of quinolone derivative was removed by multiple ethanol precipitation and the resulting beacon constructs were purified either by polyacrylamide gel electrophoresis (PAGE) in the presence of 8 M urea, or by reverse phase column chromatography. Typically the efficiency of derivatization was 70-80%.

Example 5

Figure 5:
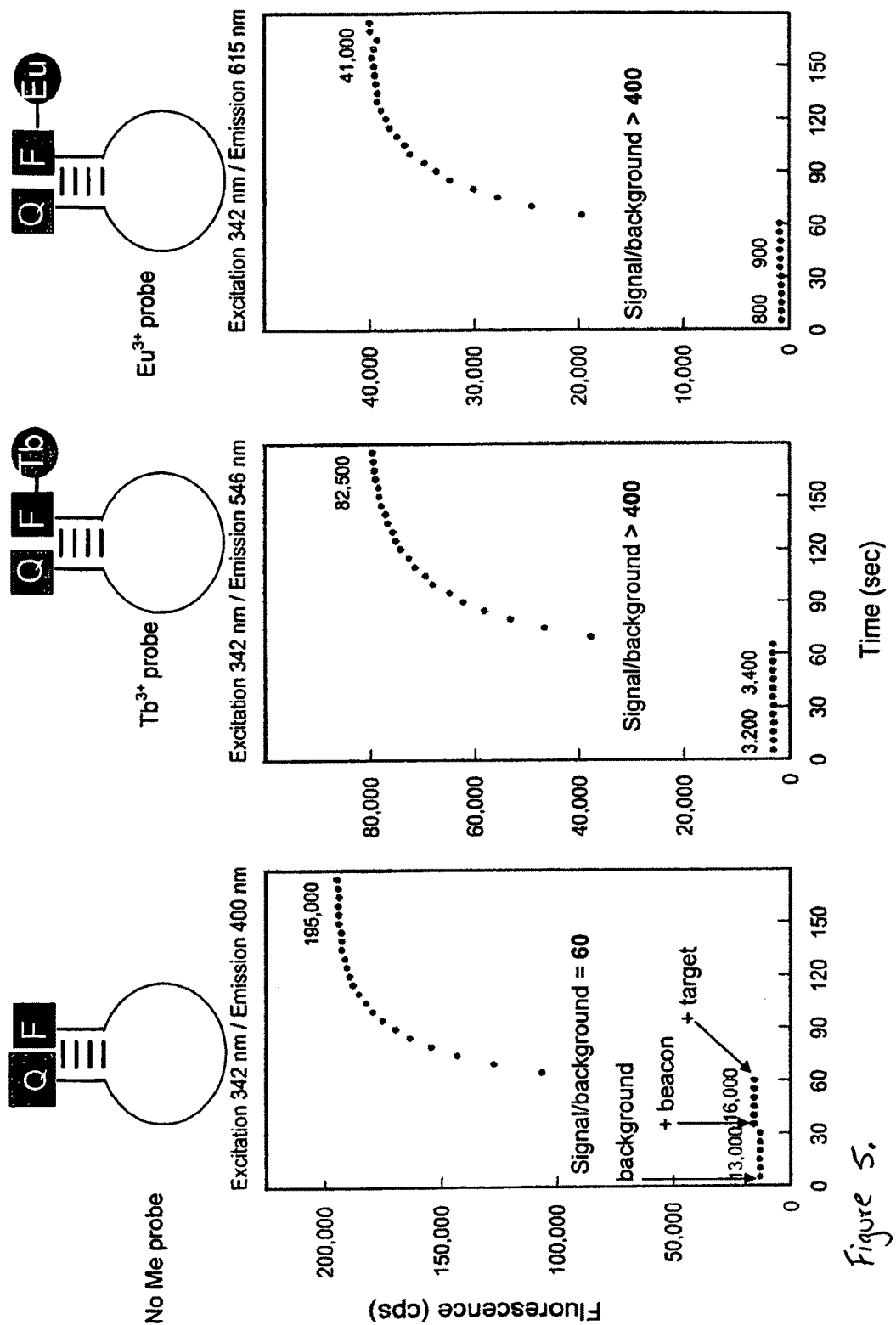
FIG. 5 is a depiction of the development of fluorescent signal of compound VII of FIG. 2 (as well as its $Eu^{3+}$ and $Tb^{3+}$ chelates) in the context of hairpin-forming hybridization probe (molecular beacon)

Fluorescent Properties of Molecular Beacons Containing 2 and 4-quinolone Derivatives FIG. 5 shows the fluorescence of the 4-quinolone based molecular beacons at different conditions. Three different 4-quinolone fluorophores were used: metal free fluorophore as well as the same fluorophore coordinated with $Tb^{3+}$ or $Eu^{3+}$. Three measurements were taken in each case. Emission of the medium without molecular beacon emission of a beacon itself and in the presence of the complementary DNA target. The emission was detected at the optimal wavelength for each fluorophore (400 nm, 546 nm and 617 nm correspondingly). It is seen, that in the absence of the target the molecular beacons possess low background fluorescence. Addition of the target caused dramatic enhancement of the fluorescent signal in all cases, evidently due to "opening" of the beacon upon hybridization with complementary DNA sequence. Notably, the enhancement factor was much higher for lanthanide based beacons (more than 400) comparing to metal free beacon (60). The extremely low emission of the metal containing forms of the molecular beacons in the absence of the target was probably due to the quenching of both fluorescence of the antenna and luminescence of lanthanide. This makes luminescent molecular beacons an excellent hybridization probes.

Example 6

Figure 6:
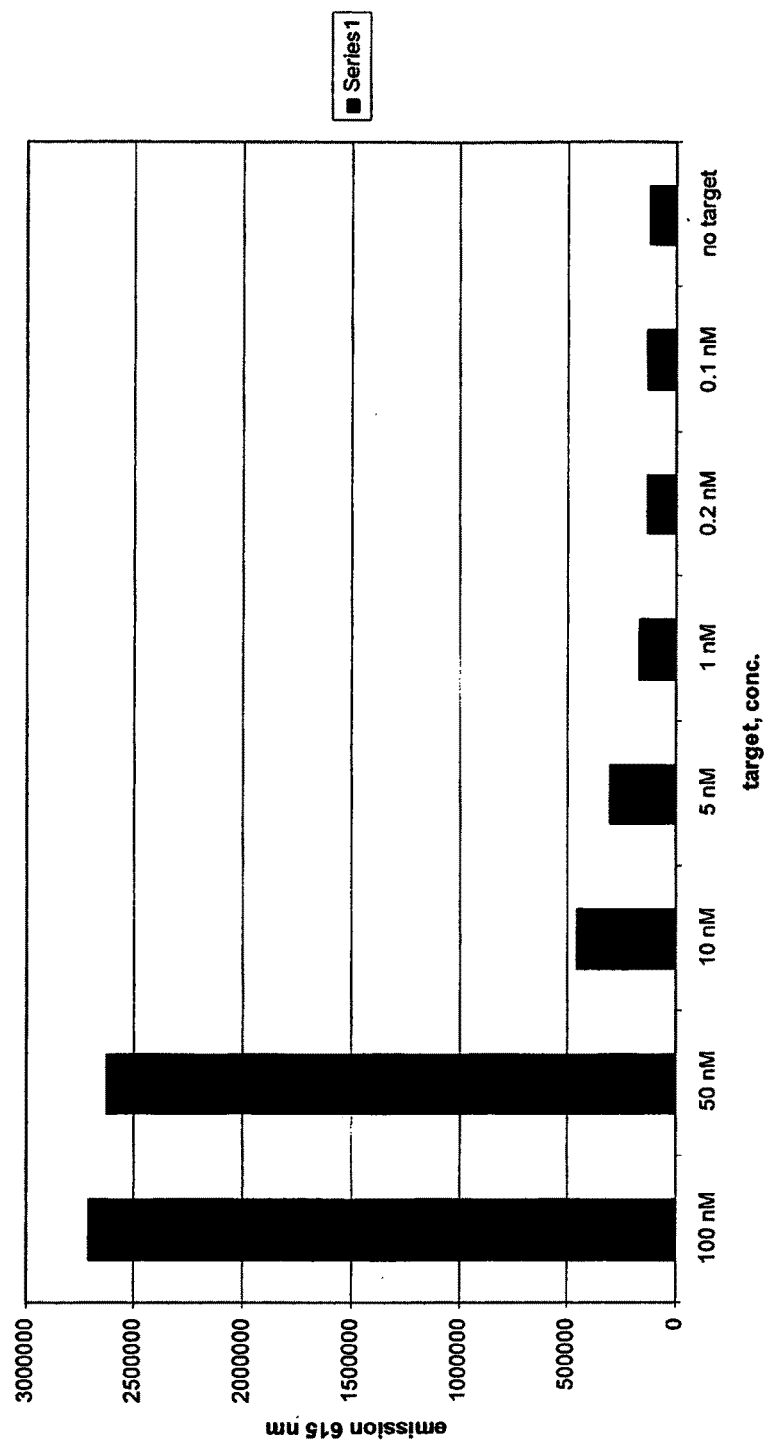
FIG. 6 is a depiction of the time-resolved emission at 615 nm of the molecular beacon (derivatized by probe VII of FIG. 3 in $Eu^{3+}$ form) in the presence of indicated concentrations of DNA target.

Time-Resolved Detection of Complementary Nucleic Acid Sequences Using Lanthanide-Based Molecular Beacons To estimate the detection limit for lanthanide based hybridization probes we measured the signal enhancement factor (in time delayed mode, 50 μs) for the molecular beacon (constant concentration 25 nM) at different concentrations of the DNA target (FIG. 6). As follows from these experiments the minimal concentration of the target that could be still reliably detected was as low as 1 nM which is better than that for conventional molecular beacons.

Example 7

The Synthesis of Ciprofloxacin Derivatives

Figure 7A:
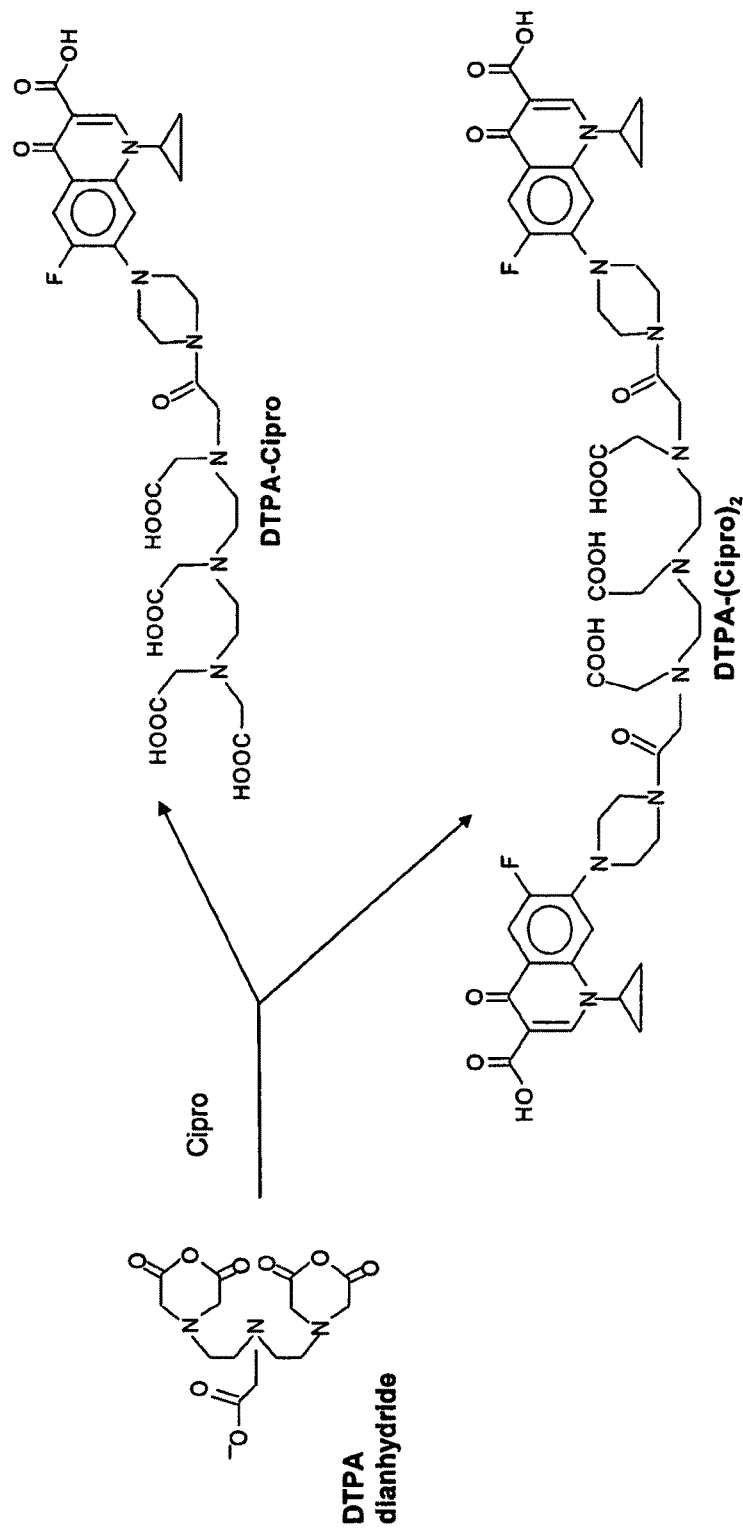
FIGS. 7a and b depict schemes for the synthesis of ciprofloxacin derivatives of dimeric luminescent chelates.
Figure 7B:
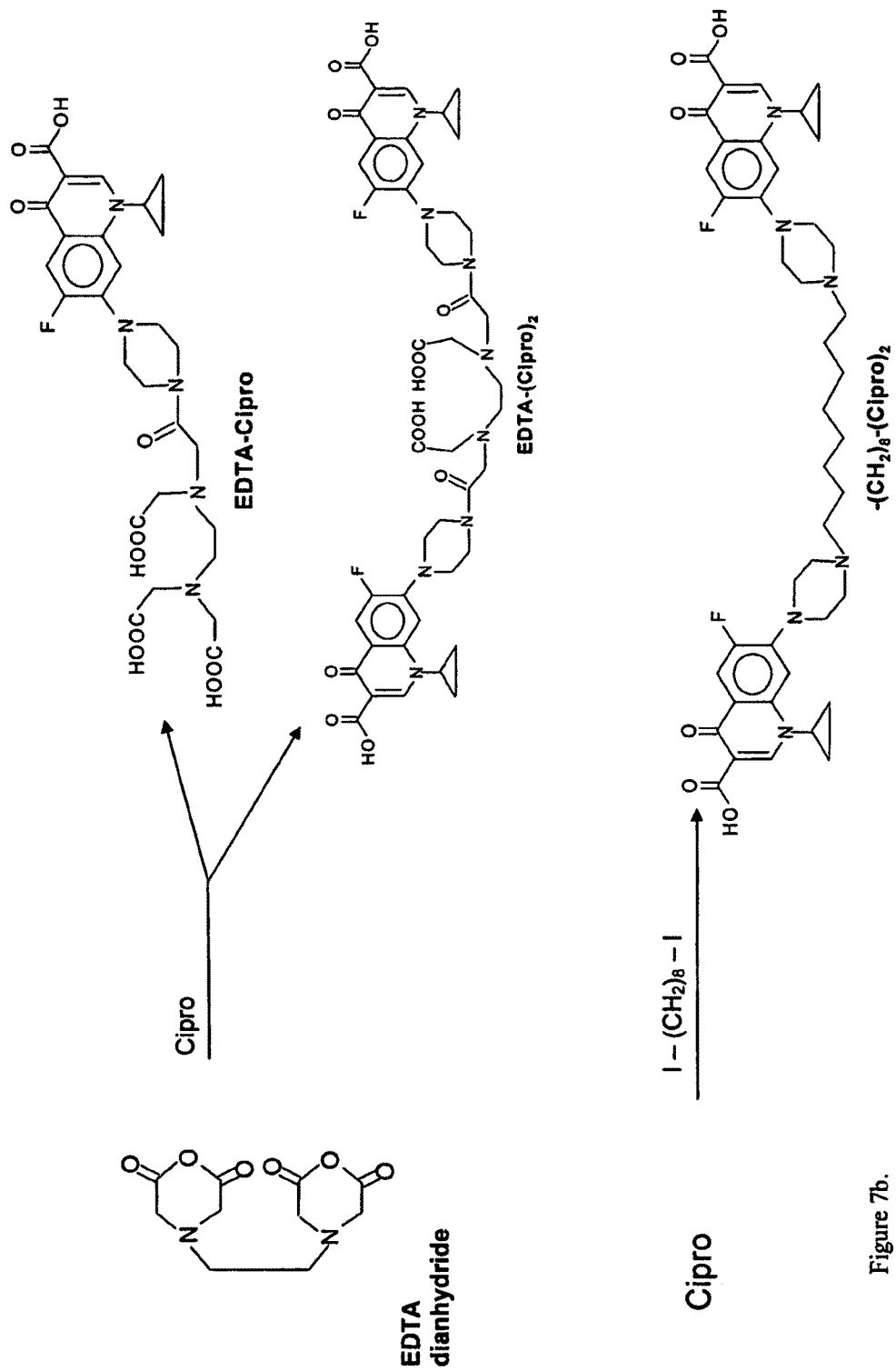

FIGS. 7a-b depict the synthetic scheme for selected lanthanide chelates. These compounds were obtained by the reaction of Ciprofloxacin (Cipro) with either EDTA or DTPA dianhydrides in dimethylformamide (DMF). Reactions in an excess of the dianhydride reagent favors the formation of monofunctional compounds (i.e., EDTA-Cipro, DTPA-Cipro), whereas bifunctional derivatives, for example, EDTA-(Cipro)$_2$ and DTPA-(Cipro)$_2$, were obtained using 2 fold molar excess of Ciprofloxacin over the indicated dianhydride. For use as a control, the bifunctional alkyl derivative compound —(CH2)$_8$-(Cipro)$_2$ was obtained by reaction of diiodooctane with Cipro. Each of the synthesized compounds was purified by silicagel chromatography and identified by UV spectroscopy.

Example 8

Figure 8:
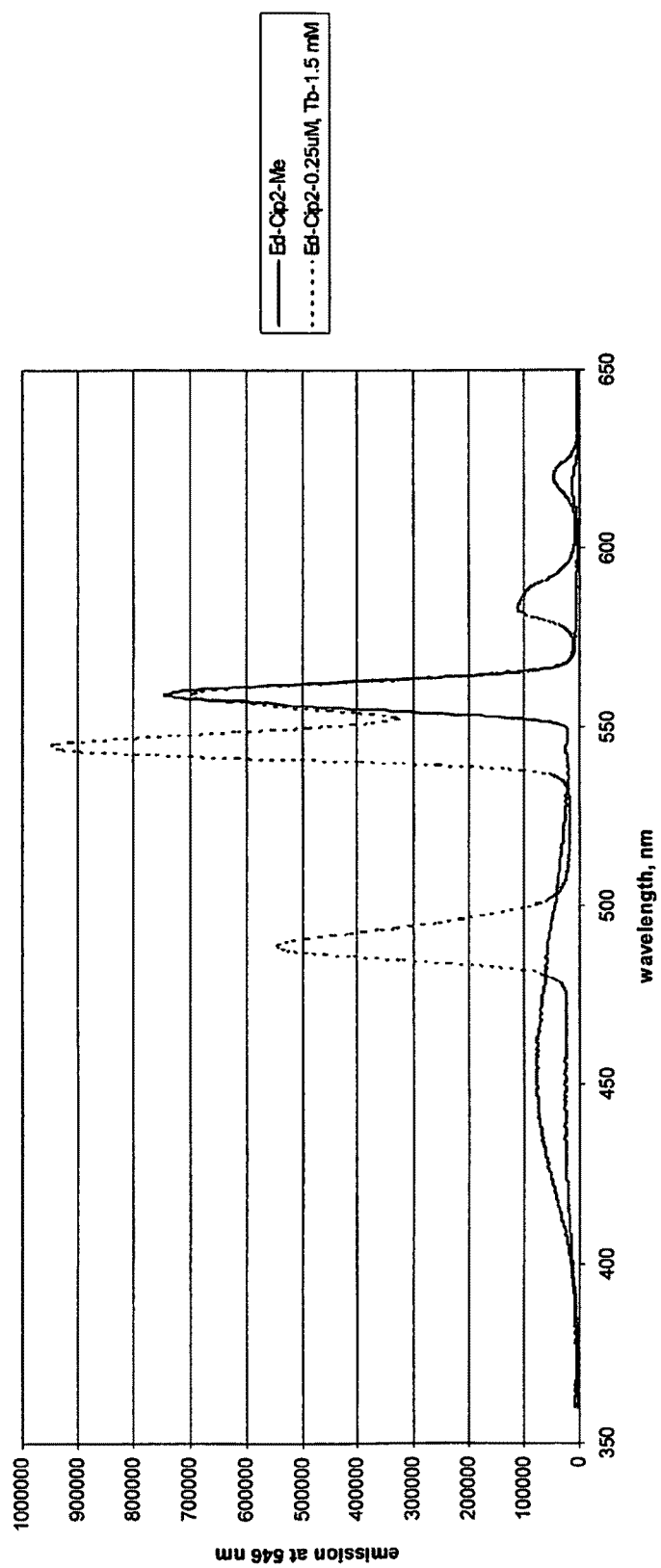
FIG. 8 is a depiction of emission spectra of EDTA-(Cipro)2 in metal free form (peak I) and in the presence of increasing concentrations of $Tb^{3+}$. Peaks II, III, V and VI correspond to Th3+ emission, peak IV—false peak (device emission)
Figure 10B:
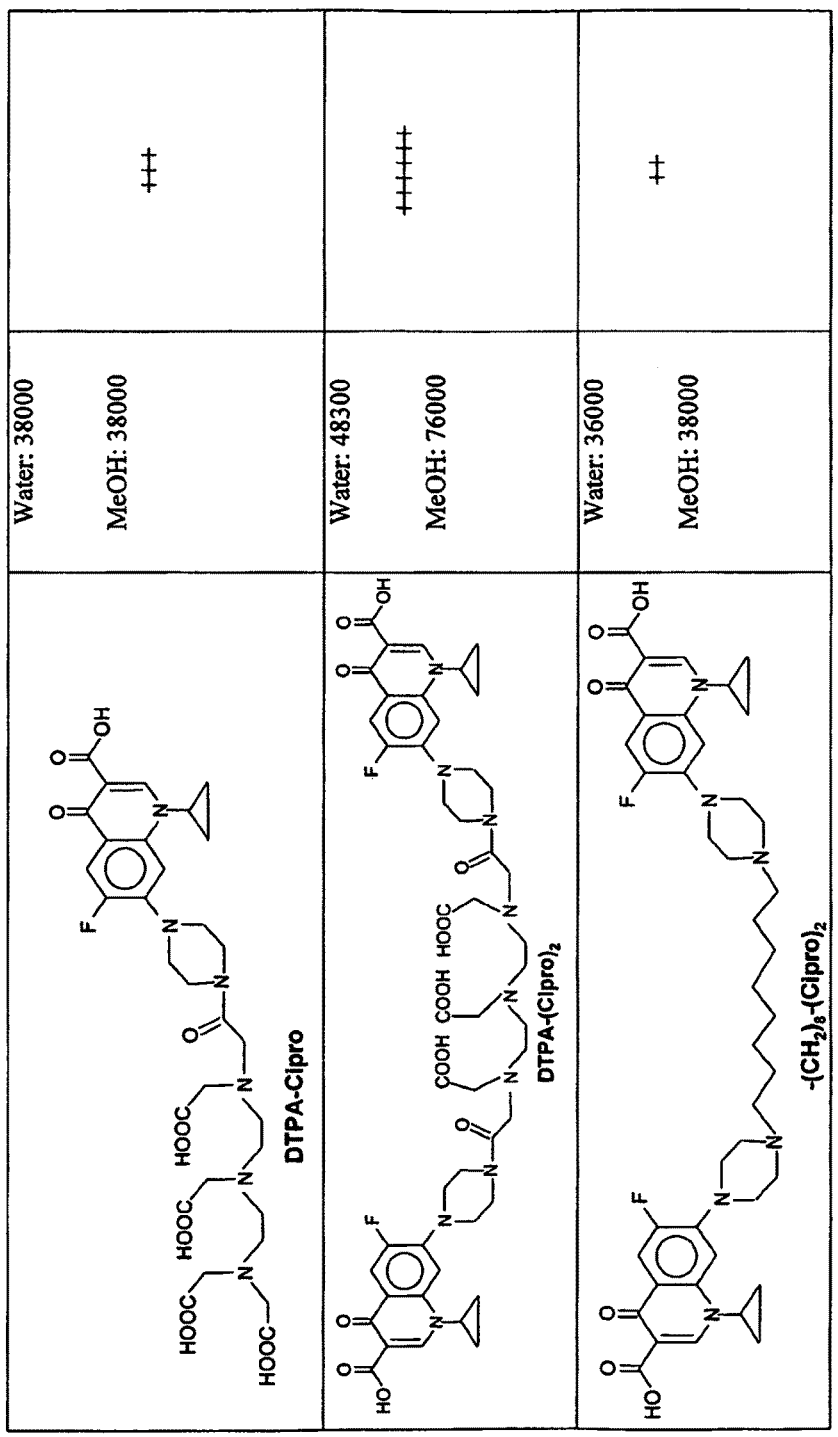
FIGS. 10a and b are a table providing UV absorption values (molar extinction units) of selected sensitizer moieties in different solvents.

Fluorescent Properties of Ciprofloxacin Derivatives and their $Tb^{3+}$ Chelates A combination of Cipro derivatives (at a concentration of 0.1 mM) with a $Tb^{3+}$ salt (at a concentration of 1 mM) in aqueous solution causes a marked decrease in the self-fluorescence of Cipro (which is blue) and the development of a green luminescence typical for Tb emission (FIG. 8). The intensity of lanthanide emission in this system was unusually high which was according to the measurements due to both high efficiency of energy transfer from antenna to Lanthanide (>90%) and high quantum yield of lanthanide emission. While the invention is not limited by any particular mechanism of action, it is believed that the observed spectral shift was due to the coordination of the lanthanide atom by the Cipro derivative, and a resultant energy transfer from Cipro fluorophore to the metal. FIGS. 10a-b show that the Cipro molecule itself is capable of causing sensitized emission of Tb; however, the intensity of the emission was weak. The intensity of the emissions from $Tb^{3+}$ complexes with monofunctional derivatives EDTA-Cipro or DTPA-Cipro was significantly higher. As indicated in FIGS. 10a-b, the highest intensity emissions (i.e., the brightest) complexes were $Tb^{3+}$ complexes with bifunctional derivatives, EDTA-(Cipro)$_2$ and DTPA-(Cipro)$_2$.

The chelating nature of the bridge, or linker, connecting the two Cipro residues was crucial for the high intensity of luminescence, since the control compound, —(CH$_2$)$_8$-(Cipro)$_2$, lacking the chelating group in the spacer, was only moderately bright in comparison to the Cipro compounds with chelating groups.

Example 9

Figure 9A:
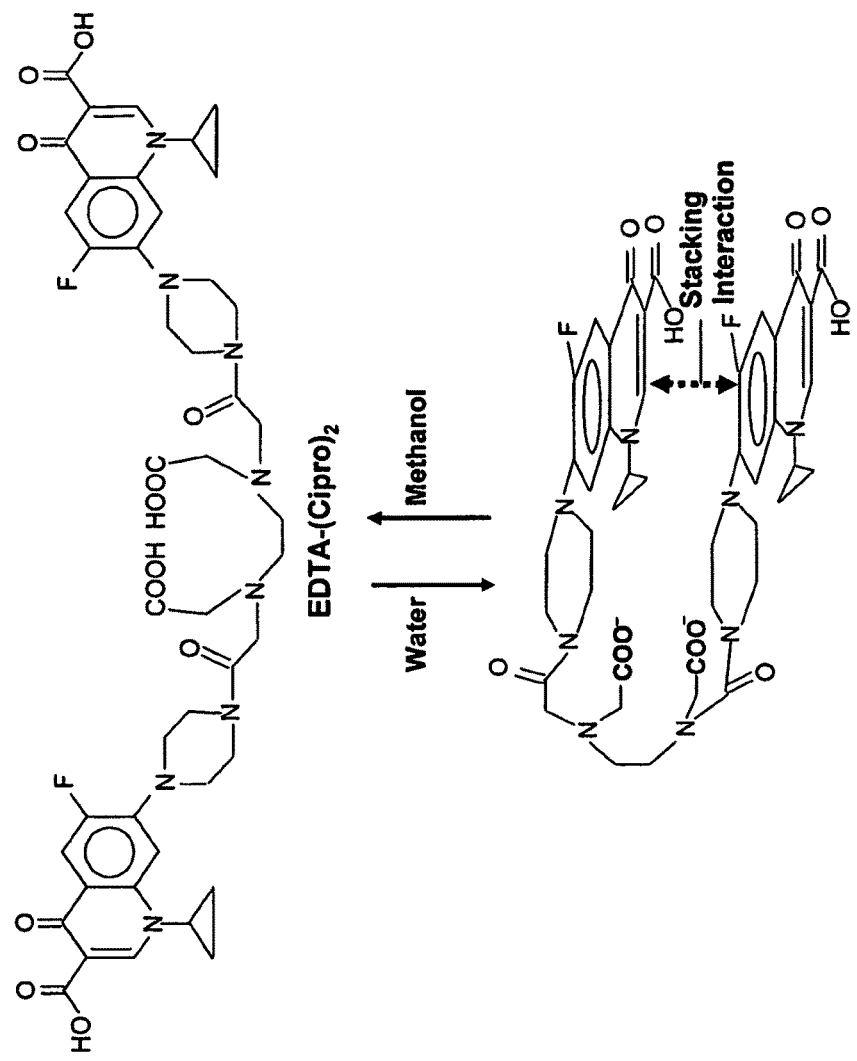
FIGS. 9a and b depict possible conformations of dimeric ciprofloxacin-chelates and their complexes in different solutions. Stacking interactions are indicated at the right with dashed, double-headed arrow.
Figure 9B:
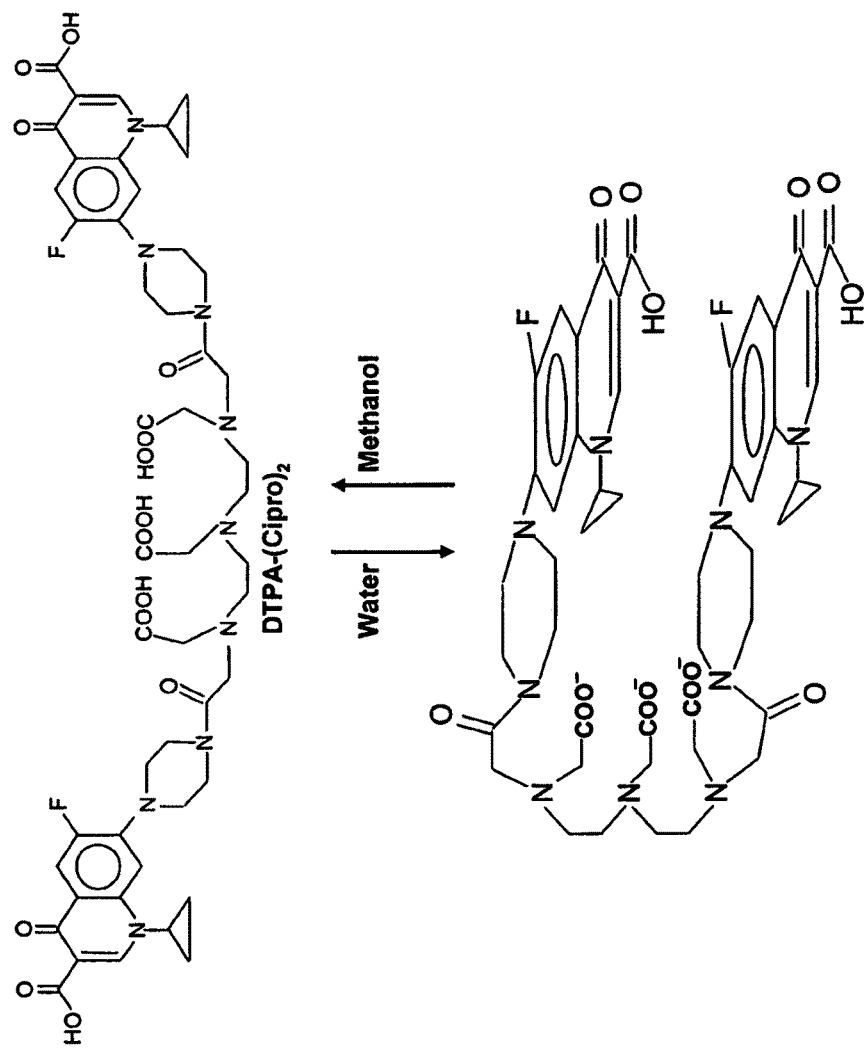
Figure 11A:
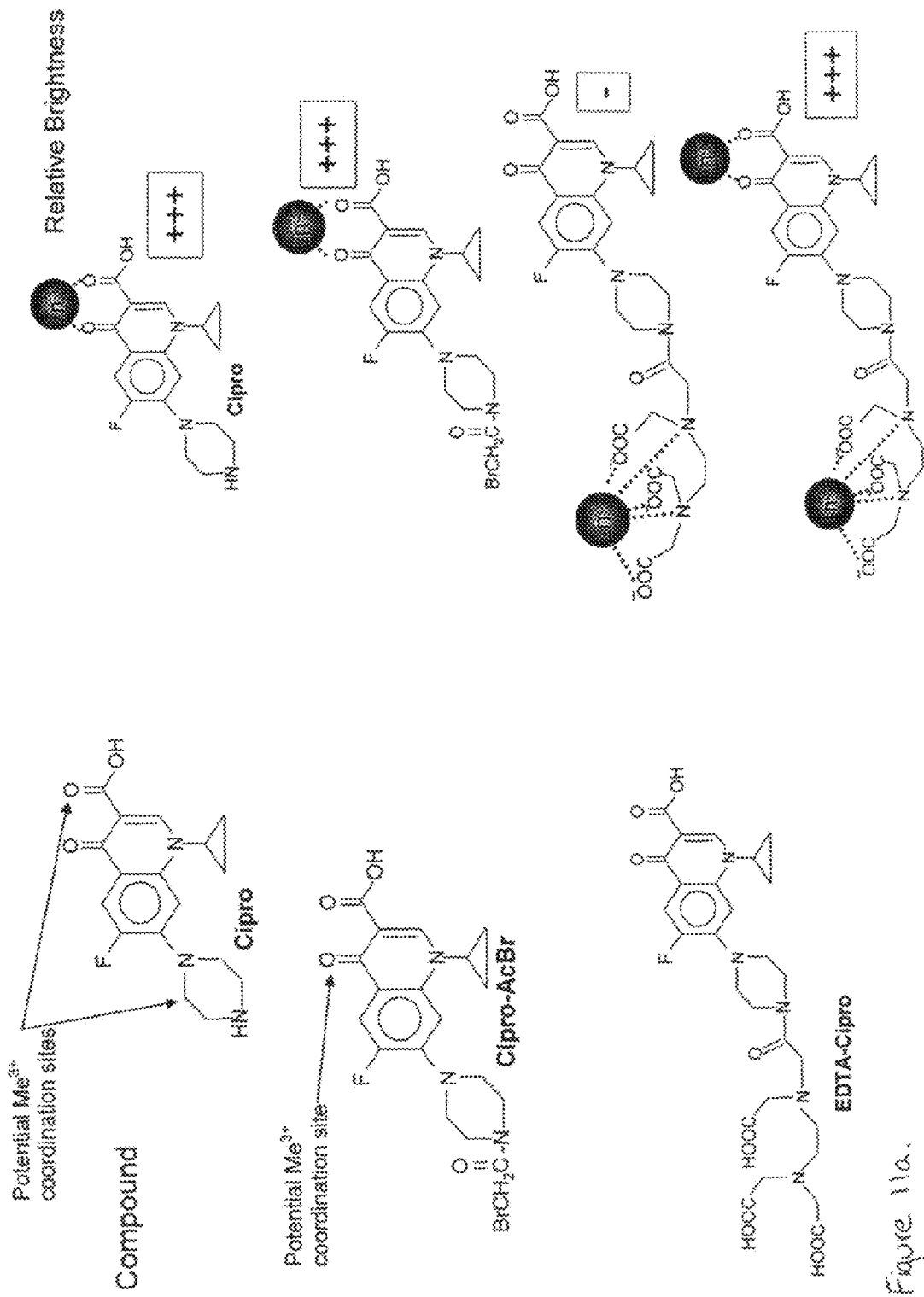
FIGS. 11a-c provide signal intensities of selected sensitizer moieties and corresponding $Ln^{3+}$ complexes.
Figure 11B:
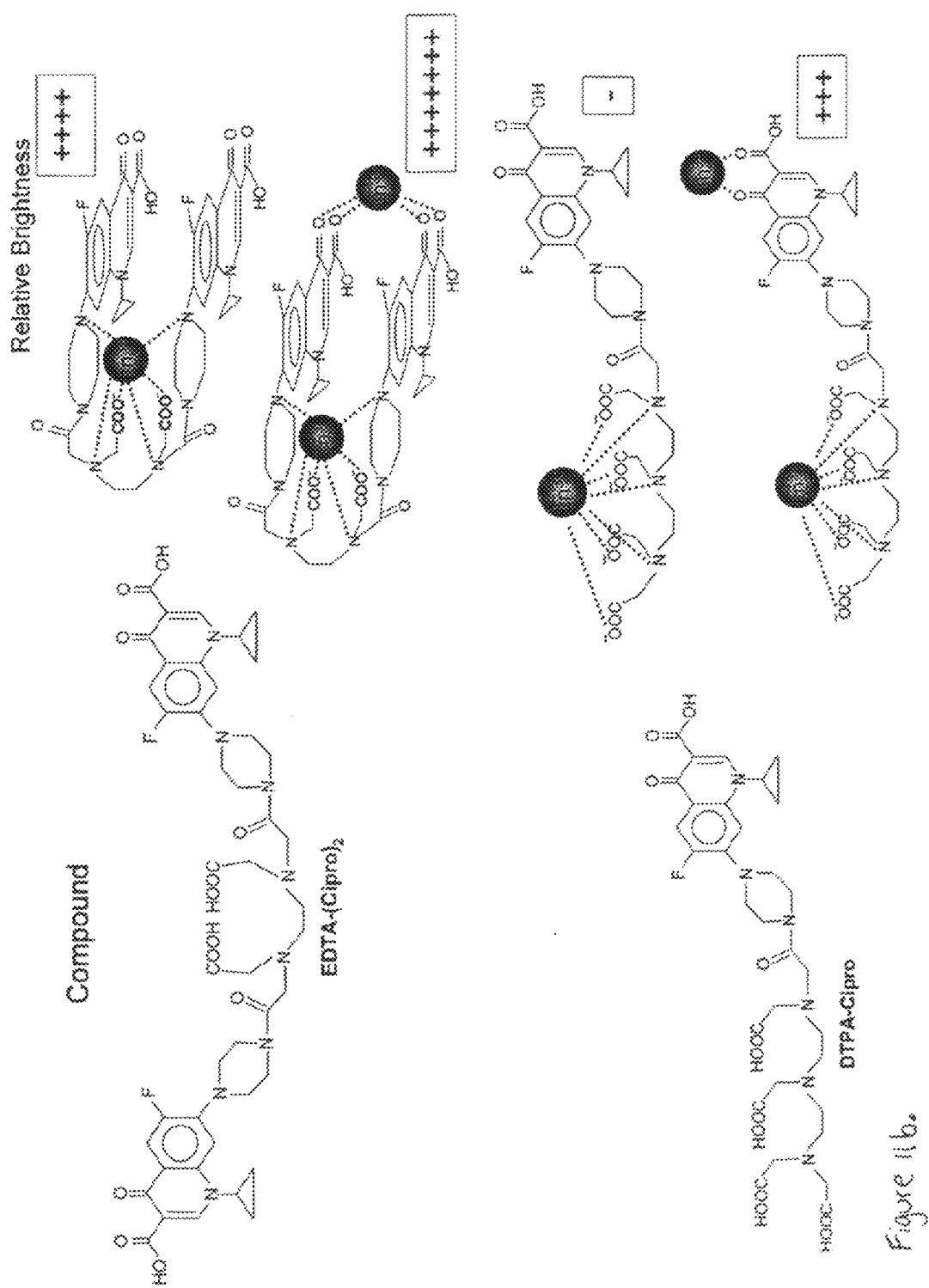
Figure 11C:
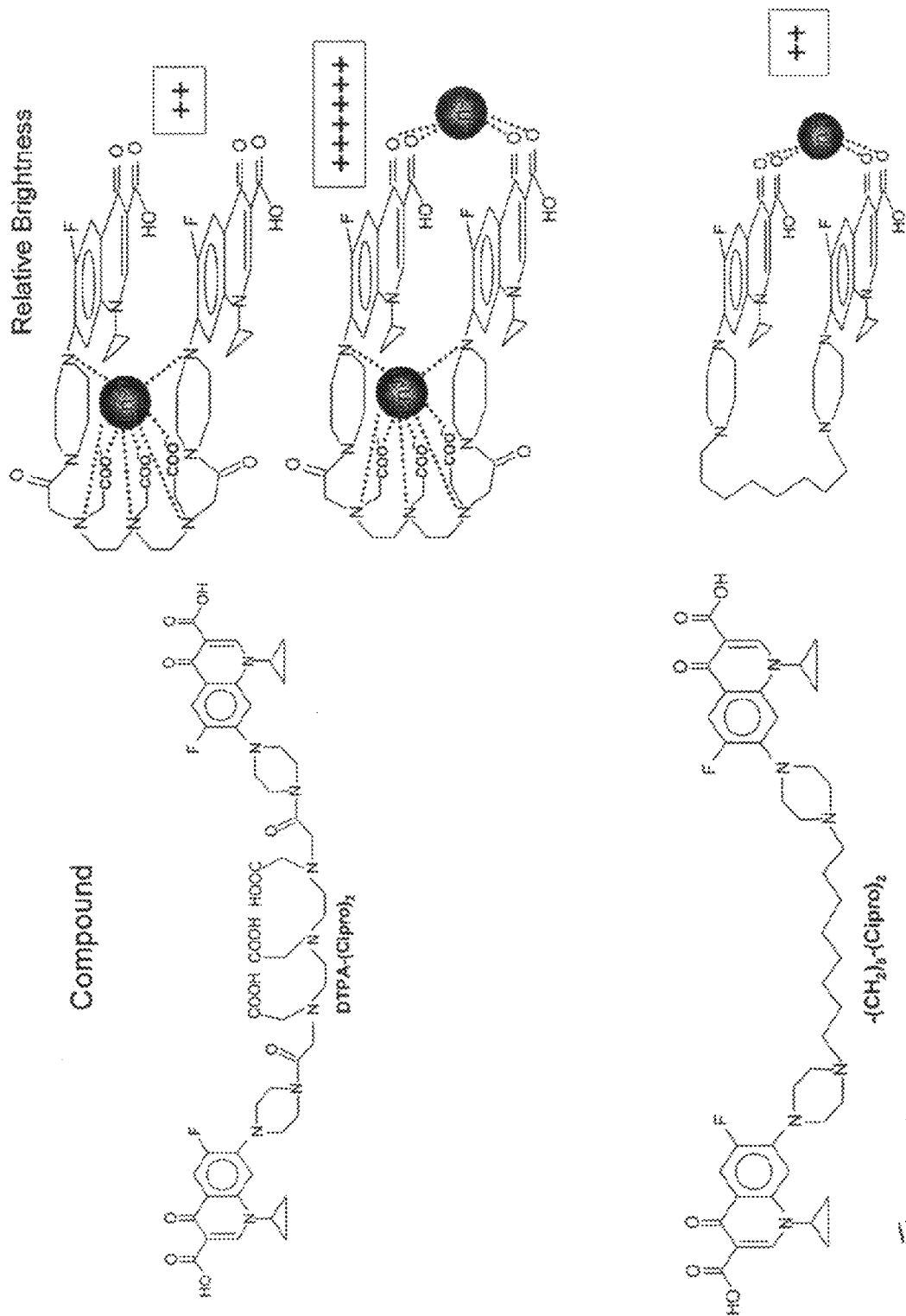

Potential Structure of Bifunctional Ciprofloxacin Chelates and their Lanthanide Complexes One reason for the high luminescence intensity of lanthanide chelates of EDTA-(Cipro)$_2$ and DTPA-(Cipro)$_2$ comes from the structure of the corresponding metal-fluorophore complexes. As evidenced from UV spectroscopy data, the molar absorbance of metal-free EDTA-(Cipro)$_2$ and DTPA-(Cipro)$_2$ compounds in water was significantly lower than in methanol (FIGS. 10a-b). This indicates that there is a hydrophobic stacking interaction between the two Cipro residues in the bifunctional compounds in water solution (FIGS. 9a-b). The absorbance in methanol is expected to increases due to disruption of the stacking. Indeed, as shown in FIGS. 10a-b, the light absorption for Cipro as well as for its monofunctional derivatives EDTA-Cipro and DTPA-Cipro was nearly the same both in water and methanol, suggesting the lack of stacking for the later compounds. The stacking of the bifunctional compounds is favored by proximation of the Cipro residues due to tethering (i.e., a covalent linkage that keeps the two moieties in close association). The proposed spatial structure of the Cipro compounds and their lanthanide complexes are shown in FIGS. 11a-c. Cipro has two potential coordination sites one formed by 3-carboxyl- and 4-oxo-groups of the ring and another one formed by 7-piperazine substituent. To determine which site is involved in the coordination of the $Tb^{3+}$ ion, we used a control compound where a potential piperazine coordination site was inactivated by acylation (Cipro-AcBr). However, this modification did not effect the development of $Tb^{3+}$ emission upon the complexation, suggesting the binding of the metal at the alternative site (see FIGS. 11a-c). The EDTA-Cipro and DTPA-Cipro compounds can form mono- and bimetallic complexes, depending on the amount of trivalent metal ($Me^{3+}$) added. One $Me^{3+}$ can bind at the a coordination site within the Cipro moeity, while the second $Me^{3+}$ can be coordinated by the chelating moiety linking the two Cipro moieties together, for example, the EDTA (or DTPA) moiety. Indeed, titration experiments demonstrated that addition of one equivalent of $Tb^{3+}$ to these compounds did not affect Cipro fluorescence, nor did it cause luminescent emission of $Tb^{3+}$ (FIGS. 11a-c). One potential explanation for this result, is that the binding affinity for the metal by EDTA (or DTPA) is much stronger than the binding affinity for the metal by the Cipro moiety itself. However, coordinated $Me^{3+}$ was not able to accept energy from the fluorophore. Further addition of the $Me^{3+}$ resulted an increased luminescence up to the level characteristic for a Cipro-$Tb^{3+}$ complex. Notably, the concentration of $Tb^{3+}$ required for maximal brightness was the same as that for Cipro-$Tb^{3+}$ complex (about 1 mM). These results indicate that there is independent binding of the two metals to the above ligands.

Different results were obtained using the bifunctional compounds EDTA-(Cipro)$_2$ and DTPA-(Cipro)$_2$. In this case, addition of the first equivalent of $Tb^{3+}$ resulted in bright luminescent complex, whereas the addition of the second equivalent of $Tb^{3+}$ further increased the brightness. Remarkably, the amount of $Tb^{3+}$ required for maximal brightness was much lower than in the case of EDTA-Cipro and DTPA-Cipro chelates, suggesting that there was a stronger coordination of the second lanthanide in the bifunctional Cipro chelates.

What is claimed is:

1. A composition of matter comprising:
   (i) a first sensitizer moiety having Formula (I) or (II);
   (ii) a chelating moiety selected from EDTA, DTPA, TTHA, DOTA, TAGA, DOTP, DTPA-BMA, DO2P, and HP-DO3A covalently joined, optionally through a first linker independently selected from —NH— and a heterocyclic alkylene moiety having the formula

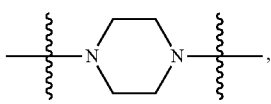

to the first sensitizer; and (iii) a second sensitizer moiety having the Formula (II) covalently joined, through a second linker having the formula

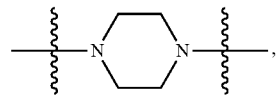

to the chelating moiety of (ii);
wherein Formula (I) is:

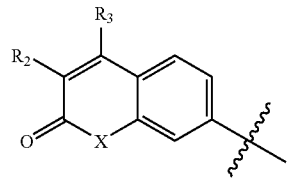

and wherein:
X is CH—R$_1$, S, or N—R$_1$;
R$_1$ is H; a linear alkylene (C$_1$-C$_{20}$), a branched alkylene (C$_3$-C$_{20}$), a cyclic alkylene (C$_3$-C$_{10}$), a linear alkenylene (C$_2$-C$_{20}$), a branched alkenylene (C$_3$-C$_{20}$), a cyclic alkenylene (C$_3$-C$_{10}$), a linear alkynylene (C$_2$-C$_{20}$), a branched alkynylene (C$_3$-C$_{20}$), a cyclic alkynylene (C$_3$-C$_{10}$), an arene (C$_6$-C$_{19}$), an alkylarene having a C$_1$-C$_{20}$ alkyl portion and a C$_6$-C$_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;
R$_2$ is H; NH$_2$; carboxamide; hydrazide; acylhydrazide or alkylhydrazide; hydroxamate; COOH; CO—R' or CO—O—R', where R' is a linear alkylene (C$_1$-C$_{20}$), a branched alkylene (C$_3$-C$_{20}$), a cyclic alkylene (C$_3$-C$_{10}$), a linear alkenylene (C$_2$-C$_{20}$), a branched alkenylene (C$_3$-C$_{20}$), a cyclic alkenylene (C$_3$-C$_{10}$), a linear alkynylene (C$_2$-C$_{20}$), a branched alkynylene (C$_3$-C$_{20}$), a cyclic alkynylene (C$_3$-C$_{10}$), an arene (C$_6$-C$_{19}$), an alkylarene having a C$_1$-C$_{20}$ alkyl portion and a C$_6$-C$_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O;
R$_3$ is a linear alkylene (C$_1$-C$_{20}$), a branched alkylene (C$_3$-C$_{20}$), a cyclic alkylene (C$_3$-C$_{10}$), a linear alkenylene (C$_2$-C$_{20}$), a branched alkenylene (C$_3$-C$_{20}$), a cyclic alkenylene (C$_3$-C$_{10}$), a linear alkynylene (C$_2$-C$_{20}$), a branched alkynylene (C$_3$-C$_{20}$), a cyclic alkynylene (C$_3$-C$_{10}$), an arene (C$_6$-C$_{19}$), an alkylarene having a C$_1$-C$_{20}$ alkyl portion and a C$_6$-C$_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms; and
wherein the

at position 7 of the phenyl ring indicates the site of covalent attachment, optionally through the first linker, of the sensitizer moiety to the chelating moiety; and wherein Formula (II) is:

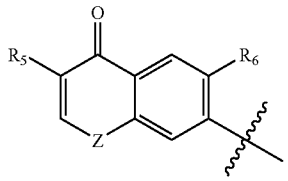

and wherein:

Z is a CH—$R_4$, S, or N—$R_4$;

$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, or alkylarene moieties are optionally further substituted with from 1-3 halo atoms;

$R_5$ is carboxamide; hydrazide; acylhydrazide or alkylhydrazide; hydroxamate; COOH; CO—R' or CO—O—R', where R' is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and $R_6$ is H; a halogen; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene or alkylarene moieties are optionally further substituted with from 1-3 halo atoms; and wherein the

at position 7 of the phenyl ring indicates the site of covalent attachment, through the second linker, of the sensitizer moiety to the chelating moiety.

2. The composition of claim 1, wherein X is N—$R_1$.
3. The composition of claim 2, wherein $R_3$ is $CH_3$.
4. The composition of claim 3, wherein said first sensitizer moiety has the formula:

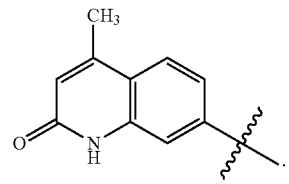 [SMILES: *c1ccc2c(C)cc(=O)[nH]c2c1]

5. The composition of claim 2, wherein $R_3$ is $CF_3$.
6. The composition of claim 5 wherein said first sensitizer moiety has the formula:

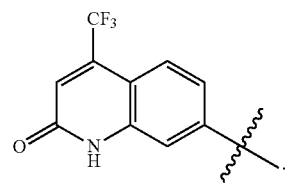 [SMILES: *c1ccc2c(C(F)(F)F)cc(=O)[nH]c2c1]

7. The composition of claim 2, wherein $R_1$ is H.
8. The composition of claim 7, wherein $R_3$ is $CF_3$.
9. The composition of claim 8, wherein said first sensitizer moiety has the formula:

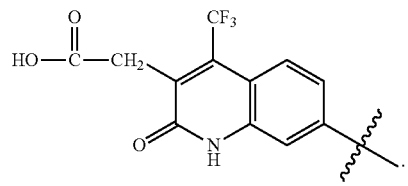 [SMILES: *c1ccc2c(C(F)(F)F)c(CC(=O)O)c(=O)[nH]c2c1]

10. The composition of claim 1, wherein the Z is N—$R_4$.
11. The composition of claim 10, wherein $R_4$ is a cyclopropyl moiety.
12. The composition of claim 11, wherein $R_5$ is an organic acid moiety having the formula COOH.
13. The composition of claim 11, wherein $R_6$ is an F atom.
14. The composition of claim 13, wherein said second sensitizer moiety has the formula:

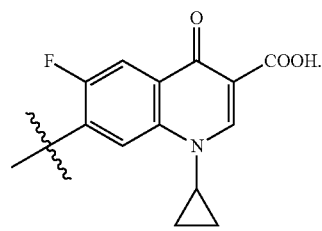 [SMILES: *c1cc2c(cc1F)c(=O)c(C(=O)O)cn2C1CC1]

15. The composition of claim 1, wherein the chelating moiety is selected from the group consisting of: TTHA, DOTA, TAGA, DOTP, DTPA-BMA, DO2P, and HP-DO3A.
16. The composition of claim 1, wherein the chelating moiety is EDTA.
17. The composition of claim 1, wherein the chelating moiety is DTPA.
18. The composition of claim 1, wherein one of the sensitizer moieties is covalently linked at the $R_2$ or $R_5$ position, optionally through a third linker moiety, to a conjugating group.

19. The composition of claim 18, wherein the conjugating group is selected from S=C=N— and Br—CH$_2$—CO—.

20. The composition of claim 1 further comprising a metal ion chelated to the chelating moiety.

21. The composition of claim 20, wherein the metal is a lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV).

22. The composition of claim 21, wherein the lanthanide is Tb(III).

23. The composition of claim 21, wherein the lanthanide is Eu(III).

24. The composition of claim 21, wherein the lanthanide is Dy(III).

25. The composition of claim 21, wherein the lanthanide is Sm(III).

26. The composition of claim 1, wherein the composition is conjugated to a macromolecule.

27. The composition of claim 26, wherein the macromolecule is a polypeptide.

28. The composition of claim 27, wherein the polypeptide is an antibody or antigen-binding fragment thereof.

29. The composition of claim 27, wherein the polypeptide is a ligand for a cellular receptor.

30. The composition of claim 27, wherein the macromolecule is a nucleic acid.

31. The composition of claim 30, wherein the nucleic acid is RNA.

32. The composition of claim 31, wherein the nucleic acid is DNA.

33. A pharmaceutical composition comprising the composition of claim 1 and a pharmaceutically acceptable carrier.

34. A pharmaceutical composition comprising the composition of claim 1 and a pharmaceutically acceptable carrier, wherein the composition of claim 1 is conjugated to an antibody or antigen-binding fragment thereof.

35. The composition of claim 13, wherein both of the first and second sensitizer moieties have the formula:

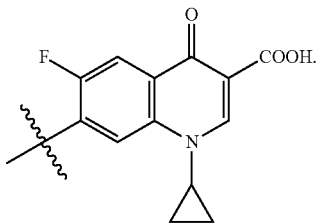 [SMILES: *c1cc2c(cc1F)c(=O)c(C(=O)O)cn2C1CC1]

* * * * *